US005994365A

United States Patent [19]
Zaworotko et al.

[11] Patent Number: 5,994,365
[45] Date of Patent: Nov. 30, 1999

[54] SUBSTITUTED DIAZAANTHRACENE COMPOUNDS HAVING PHARMACEUTICAL UTILITY

[75] Inventors: Michael John Zaworotko, Hubbards; Subramanian Sethuraman Iyer, Victoria, both of Canada

[73] Assignee: Diazans Limited, Halifax, Canada

[21] Appl. No.: 09/050,572

[22] Filed: Mar. 30, 1998

Related U.S. Application Data

[63] Continuation-in-part of application No. 08/805,971, Feb. 25, 1997, abandoned.

[51] Int. Cl.⁶ .................... A61K 31/44; C07D 471/04
[52] U.S. Cl. ............................. 514/292; 546/81
[58] Field of Search ................. 546/81; 574/292

[56] References Cited

U.S. PATENT DOCUMENTS

| | | | |
|---|---|---|---|
| 2,552,263 | 5/1951 | Dickey | 260/288 |
| 3,790,577 | 2/1974 | Waring | 260/287 R |
| 3,862,945 | 1/1975 | Schwan | 260/286 R |
| 3,984,551 | 10/1976 | Waring | 424/248 |
| 4,335,130 | 6/1982 | Schwan et al. | 424/258 |
| 4,341,784 | 7/1982 | Matsumoto et al. | 424/256 |
| 4,782,153 | 11/1988 | Rochat et al. | 546/81 |
| 4,977,149 | 12/1990 | Schaus | 514/210 |
| 5,091,535 | 2/1992 | Nomura et al. | 546/35 |

FOREIGN PATENT DOCUMENTS 03236388  10/1991  Japan .

OTHER PUBLICATIONS

DeVita VT, Hellman S., Rosenberg SA. Cancer. Principles and Practice of Oncology. JB Lippincott Company. Philadelphia. Toronto. pp. 144–145.
Schwan, Thomas J. and Nelson J. Miles, "The Cyclization of N,N'–Bis[2–(dialkoxy) ethyl] –p–xylene–a,a'–diamine Dihydrochloride to Pyrido [3,4–g] isoquinoline and 3,8–phenanthroline" J. Het.Chem. 1982,19, 1351–1353.
Bouaziz, Z., P. Nebois, H. Fillion, J.–P. Luche and G. Jenner, "Additions of Crotonaldehyde N,N–Dimethylhydrozone to p–Quinones under Ultra Sonic and Thermal Conditions" Tetrahedron 1995, 51, 4057–4064.
Nebois, P., S. Carneiro do Nascimento, M. Boitard, M.–H. Bartoli and H. Fillion "Synthesis and in vitro cytotoxic activity of aza–and diazaanthraquinone derivatives" Pharmazie 1994, 49, 819–821.
Bolitt, V., C. Mioskowski, S. Pulla Reddy and J.R. Falck, "A convenient Synthesis of Pyrido [3,4–g] isoquinolinevia ortho–Directed Metallation/Dimerization" Synth. Comm. 1988, 388–389.
Bollitt, V, C.Miokowski, R. Ominde Kollah, Sukumar Manna, D. Rajapaksa and J.R. Falck, "Total Syntesis of Vineomycinone B2 Methyl Ester via Double Bradsher Cyclization" J. Chem. Soc. 1991, 113, 6320–6321.
114:185292k, Chemical Abstracts, 1991.
115:158974y, Chemical Abstracts, 1991.
114:143154m, Chemical Abstracts, 1991.

*Primary Examiner*—Evelyn Mei Huang
*Attorney, Agent, or Firm*—Clifford W. Browning; Woodard, Emhardt, Naughton, Moriarty & McNett

[57] ABSTRACT

Novel diazaanthracenes of formula

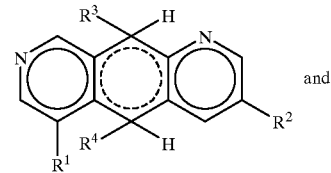

(I)

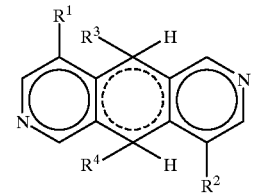

(II)

wherein the dotted line in the central ring indicates that either the central ring is aromatically unsaturated, and in this case either $R^3$ or H is absent from the 10-position and either $R^4$ or H is absent from the 5-position, or the central ring is saturated and $R^3$ and H and $R^4$ and H are present, and the corresponding 5,10-diones, N-oxides, N-halides, N-amine, salts, dimers, Diels-Alder adducts, carbene adducts and complexes with transition metal compounds display valuable antibacterial, anticancer and antifungal properties. The compounds of formulae (I) and (II) in which $R^1$ and $R^2$ are both methyl groups can be obtained by subjecting 3,5-lutidine to the effect of a strong reducing agent, for example molten sodium.

20 Claims, No Drawings

SUBSTITUTED DIAZAANTHRACENE COMPOUNDS HAVING PHARMACEUTICAL UTILITY

This is a continuation-in-part of U.S. patent application Ser. No. 08/805,971, filed Feb. 25, 1997, abandoned, the disclosure of which is incorporated herein by reference.

The present invention relates to certain novel substituted diazaanthracenes, to a novel process for preparing the substituted diazaanthracenes and to their uses as antibacterial and antifungal agents.

BACKGROUND OF THE INVENTION

Diazaanthracenes ("daas") are heterocyclic analogues of anthracene in which there are two nitrogen atoms in the anthracene framework. The anthracene framework and the numbering system used by the inventors are illustrated below:

It is remarked, however, that on some occasions the prior art uses the following numbering system:

The present invention concerns daas which have one nitrogen atom in each of the terminal or outer rings. There are only six such possible arrangements of daa, which are presented below, along with the corresponding IUPAC nomenclature and the more descriptive names preferred by the inventors.

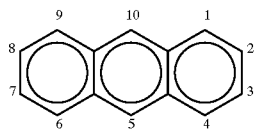

pyrido [3, 2-g] quinoline
1, 9-diazaanthracene

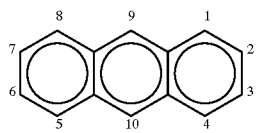

pyrido [4, 3-g] quinoline
1, 8-diazaanthracene

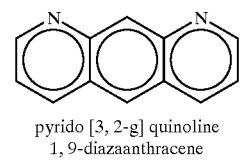

pyrido [3, 4-g] quinoline
1, 7-diazaanthracene

-continued

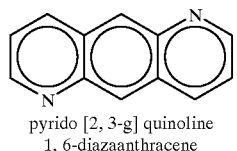

pyrido [2, 3-g] quinoline
1, 6-diazaanthracene

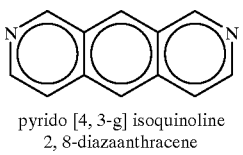

pyrido [4, 3-g] isoquinoline
2, 8-diazaanthracene

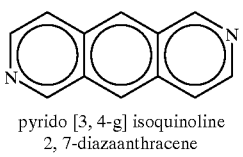

pyrido [3, 4-g] isoquinoline
2, 7-diazaanthracene

DISCUSSION OF THE PRIOR ART

Some diazaanthracenes are already known. European Patent Application No. 0 394 846, which corresponds to U.S. Pat. No. 5,091,535, discloses the compound pyrido[3,4-g]isoquinoline, the compound pyrido[2,3-g]quinoline, the compound pyrido[3,2-g]quinoline and certain 2,8-disubstituted derivatives of pyrido[3,2-g]quinoline the substituents being selected from the methyl, ethyl, propyl, butyl, carboxymethyl and carboxyethyl groups. These compounds are photochromic. They dimerize when subjected to UV radiation of wavelength about 320 to 400 nm and revert to the monomers when subjected to UV radiation of about 230 to 300 nm. These compounds are said to be valuable as memory materials. The European application also discloses the compound pyrido[4,3-g]quinoline. Page 4 of the European application purports to describe a synthesis for pyrido[2,3-g]quinoline, but the product shown has the structure pyrido[4,3-g]quinoline, not pyrido[2,3-g]quinoline. No characterizing data are given for pyrido[4,3-g]quinoline. It is stated that the pyrido[4,3-g]quinoline can be separated from pyrido[2,3-g]quinoline by liquid chromatography. EP-A 0 394 846 does not teach any utility for pyrido[4,3-g] quinoline, which is not encompassed within the claims of the application.

According to Chemical Abstracts 114:185292k and 115:158974y, Japanese Patent Applications Nos. 89/120,002 (JP 02,360,171) and 89/191,079(JP 03,56,464), respectively, disclose processes for preparing 3-pyridyl-2-(3-methylpyridyl)methanol. This is converted via 3-pyridyl-2-(3-methylpyridyl)methane to pyrido[4,3-g]quinoline, which is said to be photochromic.

Thomas J. Schwan and Nelson J. Miles, in J. Heterocylic. Chem. 1982, 19, 1351–1353, describe a synthesis of pyrido [3,4-g]isoquinoline, together with 3,8-phenanthroline, by cyclization of N,N'-bis[2-(dialkoxy)ethyl]-p-xylene-α,α'-diamine dihydrochloride. This matter is also the subject of U.S. Pat. No. 4,335,130, of Schwan and Gray, in which a mixture of pyrido[3,4-g]isoquinoline and 3,8-phenanthroline is claimed as an antifungal agent. Schwan and Miles also disclose a four-step sequence, originating with 2,5-dichloro-terephthalic dicarboxaldehyde, to the compound pyrido[3,4-g]isoquinoline.

In U.S. Pat. No. 3,862,945, of Thomas J. Schwan, 1,2,3,4,6,7,8,9-octahydro-3,8-dimethyl-4,9-diphenyl-pyrido[3,4-g]isoquinoline dihydrochloride is claimed. This patent states that the compound has an anti-parasitic activity with respect to the worm Hymenolepis nata.

Bolitt, Mioskowski, Reddy and Falck, in Synth. Comm. 1988, 388–389, refer to the work of Schwan and Miles and say that the four-step sequence of Schwan and Miles gave pyrido[3,4-g]isoquinoline in 0.7% overall yield. Bolitt et al. disclose a three-step synthesis based on a novel ortho-metallation/dimerization process that is said to provide pyrido[3,4-g]isoquinoline in 78% overall yield. The synthesis proceeded via 2,6-diaza-9,10-anthraquinone (2,7-diazaanthracene-5,10-dione), which was reduced to 5,10-dihydropyrido[3,4-g]isoquinoline by reaction with hydrogen iodide and aromatized to pyrido[3,4-g]isoquinoline by catalytic dehydrogenation. The pyrido[3,4-g]isoquinoline is required by Bolitt et al. for research to extend the scope of the Bradsher reaction, relating to the cyclo-addition of isoquinoline salts, and application of the Bradsher reaction in the total synthesis of polycyclic antibiotics is mentioned. Its use in the total synthesis of vineomycinone $B_2$ methyl ester via double Bradsher cyclization is the subject of a paper by Bolitt et al., in J. Am. Chem. Soc. 1991, 113, 6320–6321.

Fillion and co-workers, in Pharmazie 1994, 49, 819–821, report the synthesis and in vitro cytotoxic activity of diazaanthraquinone derivatives. Using the nomenclature of Fillion et al., the preparation of the compound 1,7-diaza-3-ethoxy-4-methyl-9,10-anthraquinone is described from its partially aromatized parent 1,7-diaza-3-ethoxy-1,4-dihydro-4-methyl-9,10-anthraquinone. In the nomenclature of the present inventors, the preparation of the compound 1,8-diaza-3-ethoxy-4-methyl-5,10-anthraquinone is described from its partially aromatized parent 1,8-diaza-3-ethoxy-1,4-dihydro-4-methyl-5,10-anthraquinone. However, no cytotoxic activity data are given for these two compounds. Furthermore, it should be noted that the compound 1,7-diaza-3-ethoxy-4-methyl-9,10-anthraquinone (compound 11a in Pharmazie 49 (1994)) is said by Fillion to be obtained as a component of an inseparable mixture with 1,6-diaza-3-ethoxy-4-methyl-9,10-anthraquinone (compound 11b in Pharmazie 49 (1994)).

In a later publication Fillion et al., in Tetrahedron 1995, 51, 4057–4064, describe the preparation of a series of diazaanthraquinones exploiting the Diels-Alder addition of crotonaldehyde N,N-dimethylhydrazone to azanaphthoquinones; in this manner the compound 1,7-diaza-1,4-dihydro-4-methyl-9,10-anthraquinone is prepared, using the nomenclature of Fillion et al. In the nomenclature of the present inventors this compound is 1,8-diaza-1,4-dihydro-4-methyl-5,10-anthraquinone.

SUMMARY OF THE INVENTION

In one aspect the present invention relates to novel 1,8-diazaanthracenes of formula (I)

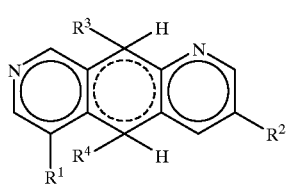

(I)

and to novel 2,7-diazaanthracenes of formula (II)

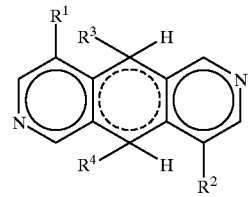

(II)

wherein the dotted line in the central ring indicates that either the central ring is aromatically unsaturated, and in this case either $R^3$ or H is absent from the 10-position and either $R^4$ or H is absent from the 5-position, or the central ring is saturated and $R^3$ and H and $R^4$ and H are present, and the corresponding 5,10-dione compounds of formula (III)

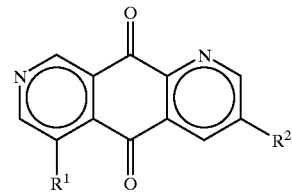

(III)

and of formula (IV)

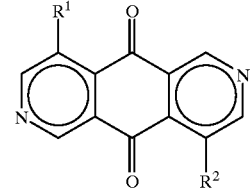

(IV)

wherein $R^1$ and $R^2$, which may be the same or different, are (a) straight chained or branched alkyl, alkenyl or alkynyl, whose carbon chain is optionally interrupted by one or several oxygen or sulphur atoms or NH groups and which is unsubstituted or is substituted by one or more cycloalkyl, aryl, halogen, cyano, hydroxyl, acyloxy, amino, acylamino, monoalkylamino, dialkylamino, alkoxy, aryloxy, aralkoxy, carbamoyl, monoalkylcarbamoyl, dialkylcarbamoyl, carboxyl, alkoxycarbonyl, acyloxycarbonyl, aralkoxycarbonyl, crown ether or porphyrin groups; (b) carboxyl; (c) alkoxycarbonyl; (d) aryloxycarbonyl; (e) aralkoxycarbonyl; (f) hydroxyl; (g) alkoxy; (h) aryloxy; (i) aralkoxy; (j) acyl; (k) acyloxy; (l) carbamoyl; (m) formyl; (n) aryl or (o) aralkyl; and $R^3$ and $R^4$, if present, may be the same or different and may be hydrogen or may take any of the values given for $R^1$ and $R^2$; and N-oxides, N-halides, N-amines, salts, dimers, Diels-Alder adducts thereof, carbene adducts thereof and also complexes with transition metal compounds.

Preferred compounds are those of formula (I) which are fully aromatic, and the 5,10-diones of those compounds. Also preferred are compounds of formula (I) in which $R^3$ and $R^4$ are both present and are both hydrogen. Mention is made particularly of 3,6-dimethyl-5,10-dihydro-1,8-diazaanthracene.

In the above definitions an alkyl, alkenyl or alkynyl group $R^1$ or $R^2$ may have up to about 18 carbon atoms, preferably up to 12 carbon atoms, more preferably up to 6 carbon atoms. Examples include methyl, ethyl, n-propyl, isopropyl, n-butyl, sec.-butyl, tert.-butyl, allyl and propargyl groups. If the carbon chain is interrupted by oxygen or sulphur atoms or NH groups it is preferred that there are up to six oxygen or sulphur atoms or NH groups. Preferred groups are ethers based on ethylene glycol, thioethers based on dimercaptoethane and polyamines based on 1,2-ethylene diamine. In monoalkylamino, dialkylamino, monoalkylcarbamoyl and dialkylcarbamoyl groups it is preferred that the alkyl groups contain up to four carbon atoms. Methyl and ethyl groups are preferred. In alkoxycarbonyl groups it is preferred that the alkoxy moiety shall have up to eight carbon atoms, especially up to four carbon atoms. As examples of aryl groups there are mentioned phenyl and naphthyl groups. As examples of aryloxy groups there are mentioned phenoxy and naphthyloxy groups and as examples of aralkoxy groups there are mentioned benzyloxy and phenylethyloxy groups. Acyl and acyloxy groups are preferably alkanoyl and alkanoyloxy groups and may contain up to eight carbon atoms, preferably up to four carbon atoms. Cycloalkyl groups may contain three to eight carbon atoms, preferably five or six carbon atoms.

Transition metal compounds that may form complexes with the diazaanthracenes of formula I include platinum and metals of the first series of transition metals, for example cobalt, iron, manganese, copper and zinc. These are used as salts, for example halide or nitrate salts.

In another aspect the invention relates to a novel process for obtaining the compounds defined above. The invention provides a process in which 3,5-lutidine is reacted with a strong reducing agent, resulting in formation of 3,6-dimethyl-1,8-diazaanthracene (1,8-DAA-3,6-(Me)$_2$) and its isomer, the compound 4,9-dimethyl-2,7-diazaanthracene. These compounds can. then be separated, if required, and if required can be subjected to further reaction, discussed below, to convert one or more of the methyl groups to the other specified values given for $R^1$ and $R^2$, or the compounds can be oxidized to the dioxo compounds or N-oxides. The compounds can be separated and then further reacted or they can be reacted and then separated, as convenient. In some instances the compounds may not be separated before being used for a particular purpose, i.e., a mixture of 1,8- and 2,7-compounds may be used.

The compound 3,5-lutidine has the structure

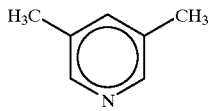

It is surprising that when this compound is subjected to strongly reducing action there are formed two isomers, 3,6-dimethyl-1,8-diazaanthracene, also known as 3,6-dimethyl-pyrido[4,3-g]quinoline, of formula

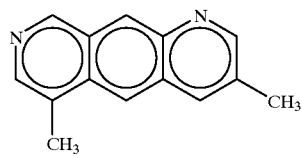

and 4,9-dimethyl-2,7-diazaanthracene, also known as 4,9-dimethyl-pyrido[3,4-g]isoquinoline, of formula

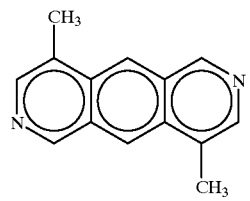

The required strongly reducing effect can be supplied for example, electrochemically. Electrochemical reduction can be effected, for example, with platinum, carbon, gold or mercury electrodes and the 3,5-lutidine dissolved in a dry polar solvent, for example acetonitrile, N,N-dimethylformamide, tetrahydrofuran or, less preferred, dioxane, and with an added electrolyte, e.g. sodium perchlorate or lithium perchlorate or a tetraalkylammonium salt, for example tetramethylammonium chloride (TMAC), tetraethylammonium bromide (TEAB), tetrapropylammonium iodide (TPAI) and tetrabutylammonium iodide (TBAI). Also mentioned are tetraalkylammonium tetrafluoroborates and tetraalkylammonium perchlorates. It is also possible to use an ionic liquid, for example a 1,3-dialkylimidazolium salt such as the acetate, nitrate or halomethylate salt. The alkyl groups of the dialkylimidazolium salt suitably contain up to three carbon atoms and particularly preferred is a salt with one methyl and one ethyl group. Alternatively, the strongly reducing effect can be supplied by a molten alkali metal, for example sodium, potassium or lithium, or a mixture of any two or three of these metals. For reasons of economy, use of molten sodium is preferred.

In a preferred embodiment, molten sodium is maintained between about 140 and 160° C., the reaction vessel is fitted with a reflux condenser and drying tube and during the course of reaction it is flushed with nitrogen or other inert gas. It is also possible to use strongly reducing metal hydrides, for example sodium hydride, to reduce lutidine to the desired compound.

The two isomers can readily be separated by, for example, flash chromatography, preparative thin-layer chromatography, preparative gas chromatography, preparative high performance liquid chromatography (HPLC) differential crystallisation or sublimation. As stated above for some uses it may be necessary to separate the isomers. For some other uses the mixture obtained directly from the reduction of 3,5-lutidine may be suitable and separation may not be required.

The dimethyl-diazaanthracene compounds that are the immediate product of the reduction of 3,5-lutidine can be converted to other compounds, i.e., compounds in which one or both of $R^1$ and $R^2$ have values other than methyl. One or both of the methyl groups can be converted to the monobromomethyl groups, for example, by reaction with the stoichiometrically appropriate amount of N-bromosuccinimide (NBS) in the presence of a catalytic amount of a free radical initiator, for example light, or benzoyl peroxide, azobisisobutyronitrile (AIBN) or di-t-butylhyponitrite. The corresponding iodides can be prepared by reaction of the bromo derivatives with sodium iodide in acetone. The mono or di-α,α'-chloromethyl derivatives can be prepared from the dimethyl compounds in a similar manner to the bromo derivatives but by using N-chlorosuccinimide instead of N-bromosuccinimide.

By selecting appropriate molar ratios of reactants it is possible to convert only one or both of the methyl groups $R^1$ and $R^2$ to, say, a bromomethyl group. For instance, use of two moles of N-bromosuccinimide with one mole of dimethyl diazaanthracene will lead to conversion of both $R^1$ and $R^2$ to bromomethyl groups. If only one mole of N-bromosuccinimide is used per mole of dimethyl diazaanthracene then there will be produced diazaanthracenes having only one bromomethyl group. In fact, there will be formed a mixture of such compounds. These can be separated, for example, by chromatography.

The bromomethyl derivatives can be subjected to further known reactions to obtain compounds having other values for $R^1$ and $R^2$. For example, they can be hydrolysed to give the corresponding compounds in which $R^1$ and $R^2$ are hydroxymethyl groups.

The bromomethyl derivatives can be reacted with a nucleophile, for example, the cyanide ion of an alkali metal cyanide such as sodium cyanide or potassium cyanide, to yield the corresponding nitrile derivative, i.e., compounds in which $R^1$ and $R^2$ are cyanomethyl groups. The nitrile groups can be hydrolyzed to yield the carboxylic acid derivatives, i.e., compounds in which $R^1$ and $R^2$ are —$CH_2COOH$ groups. Alternatively the cyanomethyl groups can be reduced to amino groups, i.e., compounds in which $R^1$ and $R^2$ are 2-aminoethyl groups. These can be alkylated in known manner, if required. The mono- or di-$\alpha,\alpha'$-bromomethyl derivatives can be oxidized directly to the aldehyde, for example by reaction with dimethylsulphoxide to give compounds in which $R^1$ or $R^2$ are formyl groups. The aldehydes are readily oxidized by known methods, for example with Jones reagent or other strong oxidizing agent, to carboxylic acid groups to give compounds in which $R^1$ or $R^2$ or both $R^1$ and $R^2$ are COOH groups. The obtained compounds in which $R^1$ or $R^2$ is $CH_2COOH$ or $R^1$ or $R^2$ is COOH can be esterified with alcohols in accordance with known procedures to convert one or more of the carboxyl groups into alkoxycarbonyl functions. Of particular interest are alkoxycarbonyl groups having up to 6, preferably up to 4 carbon atoms in the alkoxy group.

Compounds in which $R^1$ or $R^2$ or both are alkyl other than methyl can be obtained by using known chain extension reactions. For example, a daas derivative in which $R^1$ and/or $R^2$ is formyl can be reacted with a Wittig reagent e.g., $Ph_3PRBr^-$, wherein R is alkyl, preferably $C_{1-5}$, under standard conditions for the Wittig reaction, to yield the unsaturated alkyl chain adduct. The alkyl group R can be substituted so that alkylsubstituted groups $R^1$ and $R^2$ are obtained. Hydrogenation of the unsaturated alkyl chain yields the saturated chain adduct. Preferably the alkyl group $R^1$ or $R^2$ contains up to 6 carbon atoms, alkyl groups with 1 to 4 carbon atoms being particularly preferred.

For further information on methods that can be used to obtain compounds of the invention in which $R^1$ or $R^2$ are other than methyl groups reference is made to "Comprehensive Organic Transformations: a guide to functional group preparations", Larock, Richard C., VCH Publishers Inc., New York, 1989, the disclosure of which is incorporated herein by reference. For example $R^1$ and/or $R^2$ can be converted from methyl groups to carboxyl groups by methods taught by Larock. If required, carboxyl groups $R^1$ and/or $R^2$ can be converted to alkoxycarbonyl, aryloxycarbonyl or aralkoxycarbonyl groups by esterification with appropriate hydroxy-group containing reactants. Carboxyl groups $R^1$ and/or $R^2$ can be converted to carbamoyl groups by amidation. Carboxyl groups $R^1$ and/or $R^2$ can be converted directly to hydroxyl groups. Alternatively, hydroxyl groups $R^1$ and $R^2$ can be obtained by direct conversion from compounds in which $R^1$ and $R^2$ are amine or aldehyde groups. Hydroxyl groups $R^1$ and/or $R^2$ can then be converted to alkoxy, aryloxy, aralkoxy or acyloxy functional groups by, for instance, Williamson ether synthesis or by an esterification reaction. Compounds in which $R^1$ or $R^2$ contains an ether linkage, e.g., alkoxyalkyl, aryloxyalkyl or aralkoxyalkyl groups can be prepared, e.g. by ether bond formation in the known Williamson synthesis. Compounds in which $R^1$ or $R^2$ contains a carbamoyl group can be obtained by amidation of a carboxyl group present in $R^1$ or $R^2$. Compounds in which $R^1$ or $R^2$ contain an alkoxycarbonyl, aryloxycarbonyl or aralkoxycarbonyl group can be prepared by an esterification reaction between a carboxyl group present in $R^1$ or $R^2$ and an appropriate alcohol. An amine group present in a group $R^1$ or $R^2$ can be acylated in known manner.

A diazaanthracene compound of the invention can be converted to the corresponding 5,10-dione by reaction in acidic solution with an oxidizing agent. Suitable oxidizing agents include chromium trioxide, ceric ammonium sulphate and ceric anmmonium nitrate. The acidic solution causes protonation of the nitrogen atoms in the diazaanthracene and thereby prevents formation of the N-oxides. An alternative route to the 5,10-diones is by electrolytic oxidation, again under acidic conditions.

The diazaanthracenes contain two nitrogen atoms that display basic properties. These can react with acids to form acid addition salts, for instance with hydrohalic acids such as hydrogen chloride, hydrogen bromide or hydrogen iodide, with inorganic acids such as sulphuric, nitric, phosphoric, fluoroboric or perchloric acids, or with organic carboxylic acids such as formic, acetic, propionic, oxalic, succinic, sorbic, benzoic, tartaric, or also acids such as methanesulfonic acid, toluenesulfonic acid or benzenesulfonic acid. The diazaanthracenes will also form quaternary ammonium salts if reacted with alkyl halides, for example $C_{1-20}$ alkyl halides such as methyl or ethyl iodides, bromides or chlorides. One or both of the nitrogen atoms may be converted into the acid addition salt or quaternary ammonium salt. It will be appreciated that for administration to a patient any salt should be pharmaceutically acceptable, but for other purposes such as use as a synthetic intermediate or for purification other salts may be acceptable.

Salts in accordance with the invention can be acid addition salts or quaternary ammonium salts at a ring nitrogen atom or at a basic nitrogen atom in a group $R^1$ or $R^2$. In those cases where a group $R^1$ or $R^2$ carries an acidic group, for instance a carboxyl group, a salt can be formed between a base and the acidic group. In some instances there may be formed a zwitter ion.

A diazaanthracene of the formula (I) or (II) can also be converted to its corresponding N-oxide. Methods for converting amines to their N-oxides are known, for example, reaction with peracids such as m-chloroperbenzoic acid (mCPBA), peracetic acid, perbenzoic acid and the like, or reaction with sodium tungstate and hydrogen peroxide in the presence of a base or reaction with ozone.

A diazaanthracene of the formula (I) or (II) can readily be converted to the corresponding N-halide. The diazaanthracene compound is dissolved in a suitable solvent, for example acetonitrile, and a halogen, added to the solution. By this means the chloride, bromide and iodide are readily formed.

A diazaanthracene of the formula (I) or (II) can be converted to its Diels-Alder adducts by reaction with suitable dienophiles, of which norbornadiene, 3,6-dihydroxypyridazine and 4,4-dimethoxy-2,5-cyclohexadien-1-one are mentioned.

Carbene adducts can be prepared by reaction of a diazaanthracene compound with a suitable carbene compound.

For example the diazaanthracene compound can be reacted with chloroform in the present of a base such as NaOH to form the 5,10-methylene dichloride adduct. Alternatively, a diazo compound may be photolyzed or thermolyzed to cause loss of nitrogen and to generate a carbene that reacts with the DAA.

It will be appreciated that once the dimethyl diazaanthracene compound has been obtained there are many ways in which one or both of the methyl groups can be converted to other values given for $R^1$ and $R^2$ in the compounds of the invention. For instance, $R^1$ or $R^2$ groups which contain polyether or polyamine moieties can be introduced with the lithium salt of the polyether or polyamine. Many of the ways to convert from one value of $R^1$ or $R^2$ to another value are discussed above but persons skilled in the art will know of other conversions and the selection of suitable reactions or sequences of reactions for obtaining compounds of the invention without exercise of any inventive faculty will be possible, although routine testing may be required.

A compound of formula (I) in which the central ring is saturated can be obtained by reduction of a corresponding compound in which the central ring is aromatically unsaturated. One suitable reduction method is reaction with an alkali metal e.g., sodium or lithium, in the known Birch reduction, in solution in ammonia or an amine or in ammonia/tetrahydrofuran or amine/tetrahydrofuran solution, at reduced temperature. It is possible to carry out this reduction reaction in the presence of an alkyl halide and thereby introduce an alkyl group as substituent at the 5- or 10-position, or both, depending on the stoichiometry. Alkyl halides having up to seven carbon atoms are preferred. Mention is made of methyl iodide, whose presence in the reaction mixture will result in production of the 5,10-dimethyl compound or the mono-5 or mono-10 methyl compound.

A compound which is reduced and substituted in this manner can be subjected to further reactions to introduce different substituents or functional groups, to convert an alkyl group $R^3$ or $R^4$ into another group from among the possible values for $R^3$ and $R^4$. Methods discussed above in connection with $R^1$ and $R^2$ are suitable. It would, of course, be necessary to select carefully the order in which different derivatization reactions are carried out, and to use protection and deprotection of sensitive groups.

Once a compound has been reduced, e.g. by the Birch reduction, substituted at the 5- and 10-positions and, if required, further derivatized, it is possible to oxidize the compound to restore the aromatic character of the central ring. One means of aromatizing is to react with a hydrogenation catalyst, e.g. palladium or carbon in a suitable solvent such as diglyme. Another means of aromatizing is to oxidize with 2,3-dichloro-5,6-dicyano-1,4-benzoquinone (DDQ) in a suitable solvent, for example toluene or xylene. This will result in a fully aromatic molecule in which $R^3$ or $R^4$ or both is or are other than hydrogen. Compounds of formula (I) that are fully aromatic are preferred.

It will be appreciated that the chemistry applied to the diazaanthracene compound to change from one value of $R^1$, $R^2$, $R^3$ or $R^4$ to another value applies both to 3,6-dimethyl-1,8-diazaanthracene and to 4,9-dimethyl-2,7-diazaanthracene.

The compounds of the invention display a variety of interesting properties. Some known diazaanthracenes readily dimerize when irradiated with ultra violet light of wavelength of about 320 to 400 nm, and the dimers are readily converted back to the monomers by irradiation with ultra violet light of wavelength of about 230 to 300 nm. The present compounds display these same effects, which renders them useful as recording memory materials and photosensitizers. The 1,8-DAA compounds can form four isomeric photodimers. The 2,7-DAA compounds can form two isomeric photodimers. This utility is described in greater detail in European Patent Application No. 0 394 842, the disclosure of which is incorporated herein by reference.

European Patent Application No. 0 394 846 indicates that, when dimerization occurs, two bonds form between the monomer molecules, which become joined by bonds in the 5,5' and 10,10' or the 5,10' and the 5',10 positions. The compounds of this invention can also dimerize with only one bond between two monomer molecules. This invention extends to all forms of dimers that can form from monomers of the compounds of the invention.

The compounds of the invention also display antibacterial properties. They display antibacterial properties against both Gram-negative and, particularly, Gram-positive bacteria. Considerable activity against *Staphylococcus aureus*, a commonly encountered Gram-positive bacterium is demonstrated below. Activity against methicillin-resistant *Staphylococcus aureus*, and against vancomycin-susceptible- and vancomycin-resistant Enterococcus is also demonstrated below.

The compounds of the invention also display antifungal properties. *Candida albicans, Torulopsis glabrata* and *Cryptococcus neoformans* are examples of organisms for which antifungal properties have been observed. The invention therefore extends to use of the compounds of the invention for combating bacterial and fungal infections in man and other animals, and to compositions and formulations containing a compound of the invention as active ingredients in admixture with a pharmaceutically acceptable diluent or carrier. Suitable diluents or carriers and methods of preparing compositions for administration of active ingredients are well known and can be applied to the compounds of the invention.

Compounds of the invention also display in vitro antineoplastic activity against selected human cell lines.

For pharmaceutical use, the compounds of the invention may be formulated in ways that, in general, are well known to those skilled in the art. This usually involves associating the compound with a pharmaceutically acceptable carrier. Suitable forms include solutions, tablets including slow release tablets, capsules, granules, ointments, creams, sprays, suppositories, syrups, solutions or suspensions for oral administration and solutions for parenteral administration. The compounds may be administered orally, by injection including intravenous, percutaneous and subcutaneous injection, topically, including rectally or vaginally or as a spray. Typically a tablet may contain from 20 to 500 mg of active ingredient. The dose of active ingredient may vary from about 0.001 to 1 mg, preferably 0.01 to 0.5 mg per kg body weight.

The invention also extends to a commercial package containing a compound of the invention as active pharmaceutical ingredient together with instructions for its use to combat bacteria or fungi.

The compounds of the invention display polymorphism, i.e., they can assume different crystalline forms. When 1,8-DAA-3,6-(Me)$_2$ is crystallized from aqueous acetone there is formed a compound that is dark green in colour and is confirmed to be a trihydrate by single crystal X-ray crystallography. Upon sublimation, which is a preferred method of purifying 1,8-DAA-3,6-(Me)$_2$, there is formed a pale yellow compound that has been confirmed by single crystal X-ray crystallography to have no solvent of crystallization. The invention extends to all allotropes, hydrates, solvates and complexes containing a compound of the invention. Mention is made of cocrystals with weak acids, for example, fumaric and salicylic acids. Although maleic acid forms a salt with a 1,8-DAA of the invention, it is found that a 1,8-DAA and fumaric acid form cocrystals, in which 1,8-DAA as free base and the fumaric acid coexist as two separate compounds. The compounds of the invention will also form complexes with transition metal compounds, for example with PtIV compounds by reaction with potassium chloroplatinate. Such complexes form another aspect of the invention.

Depending upon the values of $R^1$ and $R^2$ and any substituents attached to the ring nitrogen atoms, a compound of the invention may contain one or more asymmetric carbon atoms, so that there may exist optical isomers of the compound. The invention extends to all such optical isomers and to mixtures of such isomers, including racemic mixtures. Methods for separating optical isomers into individual enantiomers or diastereoisomers are known to those skilled in the art.

The invention is further illustrated in the following examples illustrating the preparation and the utility of the compounds of the invention. Antibacterial and antifungal activity are demonstrated on various microorganisms, and in vitro antineoplastic activity is demonstrated against selected human cell lines.

PREPARATIVE EXAMPLES

Example 1

Synthesis of 1,8-DAA-3,6-(Me)$_2$ 1.1 Dry sodium chunks ca. 1 cm$^3$ (10 g; 0.25 mol) were added to 3,5-lutidine (35 mL; 0.31 mol) in a 2 necked 250 mL round bottomed flask equipped with a condenser and a drying tube, and a gas inlet adapter. The reaction vessel was flushed with N$_2$ for 15 minutes and maintained for 72 hours at ca. 150° C. in an oil bath to yield a black, porous, powderable solid. 100 mL methanol was added to the reaction vessel in a pressure controlled Vacuum Atmospheres Company (VAC) inert atmosphere box and allowed to stand for 24 hours. 125 mL concentrated HCl was added to the reaction mixture in a 1L beaker with stirring, allowed to cool to room temperature, and was evaporated to dryness under vacuum. 300 mL methanol (ca. 50° C.) was added to the product mixture with vigorous shaking until the product appeared entirely dissolved. The methanolic solution was cooled in an ice bath and filtered with suction to remove precipitate NaCl, and the precipitate was washed with cold methanol until the washings were colourless. The filtrate was allowed to stand over night at room temperature and filtered with suction to remove a dark green precipitate (ca.10 g). The precipitate was dissolved in a minimum of water and the aqueous solution was made alkaline by the addition of sodium hydroxide pellets and evaporated to dryness under vacuum. The solid was extracted with 100 mL acetone, filtered with suction, and washed with 5 mL acetone. 45 mL water was added to the filtrate, and the solution was cooled at −15° C. for 24 hours. The solution was filtered with suction to remove a forest green, crystalline precipitate (ca.8 g). The precipitate was sublimed under reduced pressure at ca. 100° C. in a modified sublimation apparatus to yield a pale yellow, crystalline product, identified as anhydrous 1,8-DAA-3,6-(Me)$_2$ by single crystal X-ray crystallography (P2$_1$/c; a=6.8685(8) b=21.1831(24) c=7.8727(9) β=111.9320(20); Empirical formula: C$_{14}$H$_{12}$N$_2$). The trihydrate was isolated from 20% wet acetone and confirmed to be such by single crystal X-ray crystallography (P-1; a=7.0260(20) b=10.757(11) c=10.872 (10) α=60.97(9) β=87.62(5) γ=74.02(4); Empirical formula: C$_{14}$H$_{18}$N$_2$O$_3$).

(mp 182.5° C.). $^1$H NMR (250 MHz, CDCl$_3$): δ=9.37(s, CH arom., 1H), 8.87(s, CH arom., 1H), 8.72(s, CH arom., 1H), 8.29 (s, CH arom., 1H), 8.22(8, CH arom., 1H), 8.01(s, CH arom., 1H), 2.67(s, CH 3H), 2.55(s, CH 3H); $^{13}$C NMR (250 MHz, CDCl$_3$): δ=154.88, 153.36, 143.42, 140.66, 134.33, 132.31, 131.87, 129.38, 128.78, 127.82, 126.50, 121.58, 19.21, 16.26; UV/Vis (EtOH):λ$_{max}$=388.0 nm; MS (70 eV); m/z (%): 208.12 (100) [M]$^+$; IR (KBr, [cm$^{-1}$]): 2919.3, 1821.8, 1794.0, 1623.3, 1582.0, 1530.2.

Synthesis of 1,8-DAA-3,6-(Me)$_2$.HCl 1.2 Sublimed 1,8-DAA-3,6-(Me)$_2$ was dissolved in a minimal amount of acetone, and an excess of concentrated HCl was added dropwise. A yellow precipitate formed immediately, and the solution was stirred for 15 minutes. The precipitate was filtered under suction and recrystallized from water as the trihydrate, confirmed by single crystal X-ray crystallography. (P-1; a=7.0520(8) b=10.4636(22) c=10.639(4) α=77.54(5) β=79.032(20) γ=87.841(22); Empirical formula: C$_{14}$H$_{19}$ClN$_2$O$_3$).

(mp>300° C.). $^1$H NMR (250 MHz, CDCl$_3$): δ=9.74(s, CH arom., 1H), 9.10(s, CH arom., 1H), 9.01(s, CH arom., 1H), 8.72(s, CH arom., 1H), 8.63(s, CH arom., 1H), 8.23(s, CH arom., 1H), 2.76(s, CH, 3H), 2.63(s, CH, 3H); $^{13}$C NMR (250 MHz, CDCl$_3$): δ=157.16, 150.99, 150.87, 144.38, 138.95, 138.66, 138.36, 136.27, 134.04, 130.57, 130.37, 128.25, 21.03, 18.42; UV/Vis (EtOH):λ$_{max}$=407.2 nm.

Example 2

Synthesis of 1,8-DAA-3,6-(CH$_2$X)$_2$ X=Cl,Br 2.1 1,8-DAA-3,6-(CH$_2$Br)$_2$ 2.1a NBS (N-bromosuccinimide) (171 mg, 0.96 mmol) was added to 50 mL CCl$_4$ containing 1,8-DAA-3,6-(Me)$_2$ (100 mg, 0.48 mmol) and benzoyl peroxide (11 mg, 0.045 mmol). The solution was allowed to stand for 1 hour at room temperature (RT) refluxed for 3 hours, cooled and filtered under suction. The succinimide residue was washed 3 times with small volumes of CCl$_4$. The filtrate was evaporated to dryness and washed with acetone.

72 mg (41% yield). UV/Vis (MeOH):λ$_{max}$=323.0 nm 2.1b Reactants were the same as in 2.1a without the addition of benzoyl peroxide, but the solvent was methanol, not CCl$_4$. The solution was allowed to stand at RT, exposed to direct sunlight for 1 hour and refluxed for 24 hours. The mustard coloured precipitate was filtered under suction and washed several times with 50 mL cold water to remove residual succinimide. Recrystallization from isopropanol yielded a microcrystalline precipitate.

123 mg (70% yield). UV/Vis (MeOH):λ$_{max}$=323.7 nm 2.2 1,8-DAA-3,6-(CH$_2$Cl)$_2$:

2.2a NCS (N-chlorosuccinimide) (128 mg, 0.96 mmol) was added to 50 mL CCl$_4$ containing 1,8-DAA-3,6-(Me)$_2$ (100 mg, 0.48 mmol). The solution was allowed to stand at RT, exposed to direct sunlight for 1 hour and refluxed for 24 hours. The yellow coloured precipitate was filtered under suction and washed several times with 50 mL cold water to remove residual succinimide. Recrystallization from isopropanol yielded a finely powdered precipitate.

82 mg (62% yield).

2.2b 1,8-DAA-3,6-(Me)$_2$ (100 mg, 0.48 mmol) was dissolved in 50 mL CCl$_4$ followed by the addition of 38.6 μL SO$_2$Cl$_2$ (65 mg; 0.48 mmol). The solution was allowed to reflux for 3 hours and the precipitate was collected by suction filtration. 121 mg (91% yield).

Example 3
Synthesis of 1,8-DAA-3,6-(CO$_2$H)$_2$ 3.1 1,8-DAA-3,6-(CO$_2$H)$_2$:

3.1a 1,8-DAA-3,6-(Me)$_2$ (200 mg, 0.96 mmol) was partially dissolved in 100 mL water at ca. 100° C. KMnO$_4$ (458 mg, 2.9 mmol) was then added in 10 equal portions in 10 minute intervals through a condenser equipped on a 250 mL round bottomed flask. The residual MnO$_2$ was removed by suction filtration and washed with water. The filtrate was evaporated to dryness under vacuum and 1,8-DAA-3,6-(CO$_2$H)$_2$ recrystallized from isopropanol 61 mg (24% yield).

3.1b Potassium t-butoxide (250 mg, 2.2 mmol) was dissolved in 50 mL 20% t-butyl alcohol in dimethylformamide. 1,8-DAA-3,6-(Me)$_2$ (200 mg, 0.96 mmol) was carefully added to the solution and the mixture was placed in a reaction bomb with a magnetic stir bar. The reaction vessel was flushed with oxygen for 5 minutes and the pressure was raised to 5 atm. The reaction mixture was then stirred for 30 minutes at RT, removed from the bomb, added to 50 mL ice water and extracted with 3 portions of 150 mL of CCl$_4$ in a separatory funnel. The aqueous phase was evaporated to dryness under vacuum. The expected product is the potassium salt of 1,8-DAA-3,6-(CO$_2$H)$_2$ 231 mg (67% yield).

Example 4
Synthesis of 1,8-DAA-3,6-(CH$_2$NH$_2$)$_2$: Gabriel's Method 4.1 1,8-DAA-3,6-(CH$_2$NH$_2$)$_2$: 1,8-DAA-3,6-(CH$_2$Cl)$_2$ (100 mg, 0.36 mmol) was dissolved in 100 mL hot toluene. Potassium phthalimide (133 mg, 0.72 mmol) was added and the solution was refluxed for 3 hours. The phthalimide adduct was filtered under suction and washed 3 times with a minimal amount of 60% ethanol. The bisbenzylphthalimide-1,8-DAA (100 mg, 0.20 mmol) was added to 100 mL warm 95% ethanol with 6.23 μL hydrazine hydrate (6.4 mg, 0.20 mmol). 25 mL concentrated HCl was added to the ethanolic solution and maintained at 75° C. for 1 hour. The precipitated phthalylhydrazide was filtered under suction and washed with a minimum of water. The filtrate was then evaporated to ca. 25 mL and cooled on an ice bath, filtered under suction and made alkaline with 1.0 M NaOH (pH=8.5). The aqueous solution was extracted three times with 100 mL CHCl$_3$ and the chloroform solutions were combined and evaporated to dryness under vacuum.

Example 5
Synthesis of 1,8-DAA-3,6-(Me)$_2$(N—O)$_2$ 1,8-DAA-3,6-(Me)$_2$(N—O)$_2$ 5.1 1,8-DAA-3,6-(Me)$_2$ (100 mg, 0.48 mmol) was dissolved in 50 mL CH$_3$CN, metachloroperbenzoic acid (mCPBA) (170 mg, 0.99 mmol) was added and the solution was refluxed for 18 hours. The solution was evaporated to dryness under vacuum and the solid was extracted with boiling water and cooled on an ice bath. The precipitate was filtered under suction.

97 mg (84% yield; mp>300° C.) $^1$H NMR (400 MHz, D$_2$O): δ=9.40 (s, CH arom., 1H) 8.91 (s, CH arom., 1H), 8.80 (s, CH arom., 1H), 8.34 (s, CH arom. 1H), 8.32 (s, CH arom., 1H), 8.11 (s, CH arom., 1H), 2.72 (s, CH, 3H), 2.57 (s, CH, 3H); UV/Vis(MeOH):λ$_{max}$=390.0 nm; MS (70 eV): m/z (%): 208.1(100) [M]$^+$, 224.1(24.8), 240.1(16.1).

Example 6
Synthesis of 1,8-DAA-3,6-(Me)$_2$(N—Br$_2$) 1,8-DAA-3,6-(Me)$_2$(N—Br$_2$)

6.1 1,8-DAA-3,6-(Me)$_2$ (200 mg, 0.96 mmol) was dissolved in 100 mL CH$_3$CN.50.0 μL bromine was added and a red precipitate formed immediately, the solution was cooled and filtered under suction.

307 mg (87% yield). UV/Vis(MeOH):λ$_{max}$=407.1 nm

Example 7
Synthesis of 1,8-DAA-3,6-(Me)$_2$(N—NH$_2$)$_2$ 7.1 1,8-DAA-3,6-(Me)$_2$(N—NH$_2$)$_2$ The amination of the nitrogens can be achieved with hydroxylamine O-sulphate. The synthetic route is as follows:

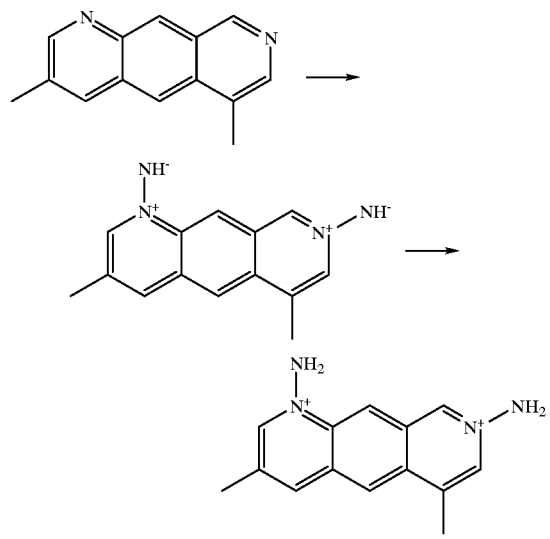

The first step was achieved by reaction of 1,8-DAA-3,6-(Me)$_2$ with hydroxylamine-sulphate (H$_2$NOSO$_3$H) with K$_2$CO$_3$ at ca. 90° C. The second step was effected by the addition of HI to the product of the first step. The product was the iodide salt of the bis-N-amine.

Example 8
General Procedure for N-alkylation

A sample of 1,8-DAA-3,6-(Me)$_2$ is dissolved in 35 mL of distilled acetonitrile. The N-alkylating agent is added to the 1,8-DAA-3,6-(Me)$_2$ solution (as an acetonitrile solution if solid, or the pure liquid if liquid). The reaction mixture is refluxed for 4–6 hrs and the product is isolated by evaporating the solvent under vacuum.

8.1 1,8-DAA-3,6-(Me)$_2$(N-Oct)

1,8-DAA-3,6-(Me)$_2$(200 mg, 0.96 mmol) was reacted with bromooctane (371 mg, 1.92 mmol) according to the general procedure.

(290 mg, 75%; looses solvent at ca. 60° C.). $^1$H NMR (250 MHz, D$_2$O): δ=9.66 (s, CH arom.), 8.82(s, CH arom.), 8.79(s, CH arom.), 8.51(s, CH arom.), 8.17(s, CH arom.), 8.08(s, CH arom.), 2.86(t, NCH), 2.67(s, CH$_3$), 2.45(s, CH$_3$), 1.99(m, CH$_2$), 1.97(m, CH$_2$), 1.22(m, CH$_2$), 1.21(m, CH$_2$), 1.20(m, CH$_2$), 1.16(m, CH$_2$), 0.64(t, CH$_3$); $^{13}$C NMR (250 MHz, CDCl$_3$): 157.30, 151.19, 144.33, 135.66, 135.17, 134.23, 133.40, 131.50, 131.29, 30.19, 125.21, 123.47, 61.48, 31.90, 31.60, 9.35, 29.16, 26.23, 22.67, 19.56, 16.95, 14.11; UV/Vis (EtOH): λ$_{max}$=369.0 nm; MS (70 eV): m/z (%): 113(1.16), 208.1(100) [M]$^+$, 321.8(0.33); IR (KBr, [cm$^{-1}$]): 2856.7, 1641.4, 1559.7.

8.2 1,8-DAA-3,6-(Me)$_2$(N-Octadec)

1,8-DAA-3,6-(Me)$_2$ (200 mg, 0.96 mmol) was reacted with bromooctadecane (642 mg, 1.92 mmol) according to the general procedure. The product was washed with ether to remove residual bromooctadecane. (253 mg, 48.6%, mp 63–65° C.). $^1$H NMR (250 MHz, CDCl$_3$): δ=11.01 (s, CH arom.), 9.39 (s, CH arom.), 9.00 (s, CH arom.), 8.62 (s, CH arom.), 8.50 (s, CH arom.), 8.28 (s, CH arom.), 5.09 (t, N—CH$_2$), 2.91 (s, CH$_3$), 2.94 (s, CH$_3$), 2.64 (m, CH$_2$), 2.15 (m, CH$_2$), 1.38 (m, CH$_2$), 1.26 (m, CH$_2$), 1.24 (m, CH$_2$), 1.19 (m, CH$_2$), 0.87 (t, CH$_3$); UV/Vis (MeOH):λ$_{max}$=383.0 nm; MS (70 eV)m/z (%): 253.3(0.56), 208.1(25.84), 42.0 (100) [M]$^+$; IR (KBr, [cm$^{-1}$]: 2917.2, 2849.2, 1643.9, 1539.8.

8.3 1,8-DAA-3,6-(Me)$_2$(N-Me)

1,8-DAA-3,6-(Me)$_2$ (200 mg, 0.96 mmol) was reacted with methyl iodide (0.12 mL, 1.92 mmol) according to the general procedure. The crude product was crystallized from water. (120 mg 35.6%; mp 128–129° C.); $^1$H NMR (400 MHz, CDCl$_3$); δ=10.68 (s, CH arom), 9.40 (s, CH arom), 9.11 (s, CH arom), 9.10 (s, CH arom), 8.61 (s, CH arom), 8.25 (s, CH arom), 2.92 (s, CH$_3$), 2.88 (s CH$_3$), 4.78 (s, N—CH$_3$). $^{13}$C NMR (400 MHz, CDCl$_3$): δ=48.90, 19.57, 16.84; UV/Vis (MeOH):λ$_{max}$=354.0 nm; MS (70 eV): m/z (%): 208.1(75.13) 223.0(0.52), 141.9(100) [M]$^+$; IR (KBr, [cm$^{-1}$]): 3020.0, 2850.5, 1619.2, 1531.6.

8.4 1,8-DAA-3,6-(Me)$_2$(N-Me)$_2$ 1,8-DAA-3,6-(Me)$_2$ (200 mg, 0.96 mmol) with trimethyloxonium (300 mg, 1.92 mmol) tetrafluoroborate according to the general procedure. The crude product was recrystallized from water and confirmed to be the N,N'-dimethyl-1,8-DAA-3,6-(Me)$_2$ tetrafluoroborate hemihydrate salt by single crystal X-ray crystallography (P2$_1$; a=7.5659(23) b=19.652(8) c=12.967(5) β=94.333(10); Empirical formula C$_{32}$H$_{38}$B$_4$F$_{16}$N$_4$O).

(491 mg, 124%; decomposes at ca. 180° C.). 1H NMR (400 MHz, D$_2$O): δ=9.82 (s, CH arom), 9.40 (s, CH arom), 9.34 (s, CH arom), 9.10 (s, CH arom), 8.99 (s, CH arom), 8.24 (s, CH arom), 4.63 (s, N—CH$_3$), 4.38 (s, N—CH$_3$), 2.75 (s, CH$_3$), 2.57(s, CH$_3$); $^{13}$C NMR (400 MHz, D$_2$O): δ=160.12, 154.35, 149.11, 139.47, 138.57, 137.47, 136.10, 135.97, 134.59, 133.25, 130.54, 129.98, 51.19, 48.42, 20.77, 18.18; UV/Vis (MeOH):λ$_{max}$=354.3 nm; IR (KBr, [cm$^{-1}$]): 3096.5, 1582.3, 1508.8.

8.5 1,8-DAA-3,6-(Me)$_2$(N-Et)

1,8-DAA-3,6-(Me)$_2$(200 mg, 0.96 mmol) was reacted with triethyloxonium hexafluorophosphate (477 mg, 1.92 mmol) according to the general procedure. The crude product was recrystallized from water.

(181 mg, 49.3%; mp 125–127° C.); $^1$H NMR (400 MHz, MeOH): δ=10.10 (s, CH arom), 9.25 (s, CH arom), 9.13 (s, CH arom), 8.95 (s, CH arom), 8.53 (s, CH arom), 8.44 (s, CH arom), 4.76 (q,CH$_2$), 2.95 (s, CH$_3$), 2.69(s. CH$_3$), 1.77 (t, CH$_3$); UV/Vis (H2O):λ$_{max}$=388.3 nm; MS (70 eV): m/z (%): 29.4(15.51), 208.0(24.22), 237.0(100) [M]$^+$; IR (KBr, [cm$^{-1}$]): 3031.8, 1622.5, 1533.7.

8.6 1,8-DAA-3,6-(Me)$_2$(N-Hex)

1,8-DAA-3,6-(Me)$_2$(200 mg, 0.96 mmol) was reacted with an excess of bromohexane (1.40 mL, 10.0 mmol) according to the general procedure.

(mp95–100° C.); $^1$H NMR (250 Mhz, CDCl$_3$): δ=10.98(s, CH arom), 9.42(s, CH arom), 9.35(s, CH arom), 8.65(s, CH arom), 8.42(s, CH arom), 8.29(s, CH arom), 5.10(m, CH$_2$), 2.90(s, CH$_3$), 2.65(s. CH$_3$), 2.18(m, CH$_2$), 1.31(m, CH$_2$), 0.85(t, CH$_3$); UV/Vis (EtOH):λ$_{max}$=355.1 nm: MS (70 eV): m/z (%): 208.0(0.08), 120.0(100) [M]$^+$; IR (Kbr, [cm$^{-1}$]): 2982.8, 2939.9, 1617.8, 1466.1.

8.7 1,8-DAA-3,6-(Me)$_2$(N-Hexadec)

1,8-DAA-3,6-(Me)$_2$(200 mg, 0.96 mmol) was reacted with an excess of bromohexadecane (2.80 mL, 9.16 mmol) according to the general procedure. The product was recrystallized from water.

(30 mg, 6.07%; mp 52° C.); $^1$H NMR (250 Mhz CDCl$_3$): δ=10.94(s, CH arom), 9.40(s, CH arom), 9.02(s, CH arom), 8.56(s. CH arom), 8.32(s, CH arom), 8.21(s, CH arom), 5.07(t, CH$_2$), 2.89(s, CH$_3$), 2.65(s, CH$_3$), 2.13(m, CH$_2$), 1.65(m, CH$_2$), 1.23(m, CH$_2$), 0.90(t, CH$_3$); MS (70 eV): m/z (%): 223.0(0.76), 208.0(100) [M]$^+$, 431.0(0.07); UV/Vis (EtOH):λ$_{max}$=355.8 nm; IR (Kbr, [cm$^{-1}$]): 2915.9, 2852.0, 1559.9, 1508.4.

8.8 1,8-DAA-3,6-(Me)$_2$(N—Pr)

1,8-DAA-3,6-(Me)$_2$(200 mg, 0.96 mmol) was reacted with an excess of bromopropane (0.872 mL, 9.6 mmol) following the general procedure outlined. Crystallization of the product from THF was attempted; however, no crystals were obtained.

Example 9

Synthesis of 1,8-DAA-3,6-(Me)$_2$ .fumaric acid 9.1 1,8-DAA-3,6-(Me)$_2$.HO$_2$CCH═CHCO$_2$H 1,8-DAA-3,6-(Me)$_2$ (100 mg, 0.48 mmol) and fumaric acid (56 mg, 0.48 nmol) were ground together with mortar and pestle and dissolved in 50 Ml acetone. This solution was allowed to reflux for 1 hour and cool for 24 hours with slow evaporation. Crystalline material was collected by suction filtration and confirmed to be the fumaric acid/1,8-DAA-3,6-(Me)$_2$ hemiacetone 1:2 cocrystal (P-1; a=8.0995(28) b=8.6333(25) c=12.236(2) α=88.498(3) β=85.152(4) γ=64.360(2); Empirical formula: C$_{35}$H$_{34}$N$_4$O$_5$). The filtrate was evaporated to dryness under vacuum to yield a less crystalline product.

(quantitative yield; mp 216–220° C.). $^1$H NMR (250 Mhz, D$_2$O): δ=9.38(s, CH arom., 1H), 8.90(s, CH arom., 1H), 8.01(s, Ch arom., 1H), 8.57(s, CH arom., 1H), 8.34(s, CH arom., 1H), 8.23(s, CH arom., 1H), 6.71(s, ═CH, 2H), 2.75(s, CH, 3H), 2.60(s, CH, 3H), 2.15(s, CH, 2H); UV/Vis (MeOH):λ$_{max}$=369.2 nm; IR (KBr, [cm$^{-1}$]) 3032.8, 2370.6, 1711.4, 915.8.

Example 10

Synthesis of 1,8-DAA-3,6-(Me)$_2$.Maleic anhydride 10.1 1,8-DAA-3,6-(Me)$_2$.OC(O)CH═CHC(O)

1,8-DAA-3,6-(Me)$_2$ (100 mg, 0.48 mmol) and maleic anhydride (47 mg, 0.48 mmol) were each dissolved in 2 mL of anhydrous acetonitrile. The solutions were combined and refluxed for 24 hours. A gelatinous precipitate was collected by decanting the mother liquor.

(mp>300° C.). UV/Vis (MeOH):λ$_{max}$=445.9 nm; IR (KBr, [cm$^{-1}$]) 1718.1 (C═O).

Example 11

Synthesis of 1,8-DAA-3,6-(Me)$_2$.maleic acid 11.1 1,8-DAA-3,6-(Me)$_2$.HO$_2$CH═CHCO$_2$H 1,8-DAA-3,6-(Me)$_2$(100 mg, 0.48 mmol) and maleic acid (53 mg, 0.46 mmol) were ground together with mortar and pestle and dissolved in 50 mL acetone. This solution was allowed to reflux for 1 hour and cool for 24 hours with slow evaporation. Crystalline material was collected by suction filtration and the filtrate evaporated to dryness under vacuum to yield a less crystalline product confirmed to be the maleic acid/1,8-DAA-3,6(Me)$_2$ 1:1 acid addition salt (P2$_1$/c; a=8.4229(9) b=11.6946(16) c=16.6946(24) β=96.8270(0); Empirical formula: C$_{18}$H$_{16}$N$_2$O$_4$).

(quantitative yield; mp 158–161° C.). $^1$H NMR (250 MHz, d$_4$-MeOH): δ=9.58(s, CH arom., 1H), 8.96(s, CH arom., 1H), 8.94(s, CH arom., 1H), 8.65(s, CH arom., 1H), 8.36 (s, CH arom., 1H), 8.24(s, CH arom., 1H), 6.26(s, ═CH, 2H), 2.80(s, CH, 3H), 2.61(s, CH, 3H), 2.14(s, CH, 2H); UV/Vis (MeOH):λ$_{max}$=351.4 nm; IR (KBr, [cm$^{-1}$]) 3076.2, 2364.8, 1684.8, 1384.2.

Example 12

Synthesis of 1,8-DAA-3,6(Me)$_2$.norbornadiene

12.1 1,8-DAA-3,6-(Me)$_2$.norbornadiene 1,8-DAA-3,6-(Me)$_2$ (100 mg, 0.48 mmol) and norbornadiene (52 mg, 0.56 nmol) were each dissolved in 25 mL of anhydrous acetonitrile. The solutions were combined and refluxed for 24 hours. The product was collected by gravity filtration and recrystallized from acetone.

(mp 125–129° C.). $^1$H nmr (250 MHz, d$_4$-MeOH): δ=9.40 (s, CH arom., 1H), 8.91(s, CH arom., 1H), 8.90(s, CH arom., 1H), 8.78 (s, CH arom. 1H), 8.38(s, CH arom., 1H), 8.10(s, CH arom., 1H), 2.71 (s, CH, 3H), 2.59(s, CH, 3H); UV/Vis (MeOH):λ$_{max}$=351.4 nm; IR (KBr, [cm$^{-1}$]) 3076.2, 2364.8, 1684.8, 1384.2.

Example 13

Adduct of 1,8-DAA-3,6-(Me)$_2$ and K$_2$PtC$_4$

13.1 1,8-DAA(Me)$_2$.HCl (242 mg; 0.99 mmol) and K$_2$PtCl$_4$ were each dissolved in 20 mL water at 60° C. and the solutions were combined and allowed to cool to room temperature. A red precipitate was filtered under suction and washed with cold water.

Example 14

1,8-DAA-3,6-(Me)$_2$-5,10-(O)$_2$

Chromium trioxide (426 mg; 4.25 mmol) was dissolved in 0.4 mL of water and added to 1.0 mL glacial acetic acid. This solution was added dropwise to a solution of 1,8-DAA-3, 6-(Me)$_2$ (250 mg; 1.2 mmol) in 12.5 mL glacial acetic acid and was refluxed for 10 minutes. The reaction mixture was filtered and the filtrate was adjusted to a pH of approximately 11 with 10 N sodium hydroxide. This was filtered to yield a highly colored precipitate, which was dried and purified by flash liquid chromatography.

$^1$H nmr (250 MHz, CDCl$_3$): δ=9.54 (s, CH, arom.), 8.97 (s, CH, arom.), 8.93 (s, CH, arom.), 8.37 (s, CH, arom.), 2.84 (s, CH$_3$), 2.68 (s, CH$_3$); GC/MS (70 eV):m/z(%): 154, 182, 210, 238 [M$^+$].

Example 15

Dimer Compound 5,10-dihydro-1,8-DAA-3,6-(Me)$_2$ (50 g; 0.24 mmol) was dissolved in 20 mL methanol and allowed to stand at 22° C. for 30 days. The progress of the reaction was monitored every 2 days by TLC. At the conclusion of the experiment, the 5,10-dihydro-1,8-DAA-3,6-(Me)$_2$ had been completely consumed, and three products were separated from the reaction mixture by preparative TLC. Two of the products have been confirmed to be the 1,8-DAA-3,6-(Me)$_2$ and the 1,8-DAA-3,6-(Me)$_2$-5,10-(O)$_2$. The third product has been shown to have the empirical formula C$_{28}$H$_{22}$N$_4$O$_2$, determined by mass spectroscopy (molecular weight: 446.51 g/mol), indicating that it is a dimer. m/z (%): 446.5 (100), 223.2 (93), 196.2 (12), 168.2 (14), 141.1 (9), 115.1 (14), 77.1 (21), 44.0 (26). The dimer has the structure:

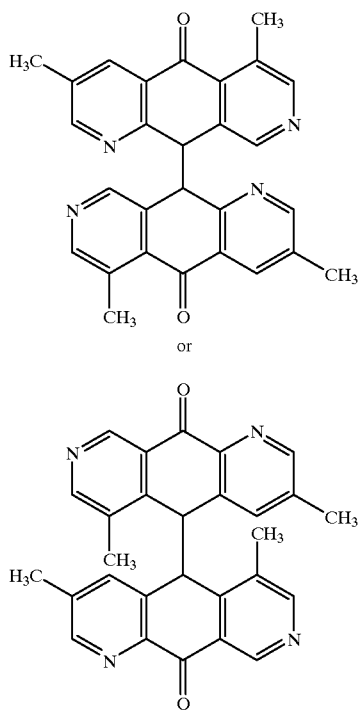

or may be a mixture of these structures. These compounds can be called 10,10'-bis(3,6-dimethyl-5,10-dihydro-1,8-diazaanthracen-5-one) and 5,5'-bis(3,6-dimethyl-5,10-dihydro-1,8-diazaanthracen-10-one), respectively.

Example 16

5,10-Dihydro-1,8-DAA-3,6-(Me)$_2$ 1,8-DAA-3,6-(Me)$_2$ (50 mg, 0.24 mmol) was dissolved in 10 mL tetrahydrofuran and added to 20 mL anhydrous ammonia at −70° C. followed by the addition of 6.5 μL (1.5 equivalents) of water. Sodium metal (15 mg; 0.65 mmol) was added to this mixture and was stirred for 30 min. The resultant mixture was then poured rapidly into a 250 mL cold dilute aqueous ammonium chloride solution to quench the reaction. This was extracted three times with 100 mL chloroform and the combined extracts were evaporated to dryness under reduced pressure. The product was confirmed by accurate mass spectroscopy and nmr analysis to be the title compound.

Example 17

2,7-DAA-4,9-(Me)$_2$

The residue, after the removal of the sublimed 1,8-DAA-3,6-(Me)$_2$ in Preparative Example 1.1, was purified by flash liquid chromatography. This yielded a product which was confirmed to be the 2,7-DAA-4,9-(Me)$_2$ isomer.

(mp 250–252° C.); $^1$H nmr (250 MHz; CDCl$_3$): δ=8.88 (s, CH, arom.), 8.65 (s, CH, arom.), 8.13 (s, CH, arom.), 2.58 (s, CH$_3$); $^{13}$C nmr (250 MHz; CDCl$_3$): δ=127.24, 135.06, 155.3; IR (KBr, [cm$^{-1}$]): 2975, 2921, 1625, 1528, 1443, 1372, 1301, 1236.

MACRODILUTION ASSAY PROTOCOL

A working antimicrobial solution was prepared by diluting the test compound in Mueller Hinton Broth (MHB) to the highest final concentration desired. The test was performed in 13×100 mm test tubes. Two mL of the working solution of test compound were added to test tube 1 of the dilution series. To each remaining tube, 1.0 mL of MHB was added. A sterile pipette was used to transfer 1.0 mL from tube 1 to tube 2. After thorough mixing 1.0 mL was transferred (with a separate pipette for this and each succeeding transfer) to tube 3. This process was continued to the next to last tube from which 1.0 mL was removed and discarded. The last tube received no antimicrobial agent and served as a growth control. The inoculum was prepared and adjusted to contain $10^5$ to $10^6$ CFU/mL by adjusting the turbidity of a broth culture to match to 0.5 McFarland standard. It was then further diluted 1:200 in broth. One mL of the adjusted inoculum was added to each test tube. The final concentrations of antimicrobial agents in this test were half those of the initial dilution series because of the addition of an equal volume of inoculum in broth. Tubes were incubated at 35° C. for 18 hours. The lowest concentration of antimicrobial agent that resulted in complete inhibition of visible growth represents the MIC. A very faint haziness or a small button is usually disregarded.

Results:

S. aureus against 1,8-DAA-3,6-(Me)$_2$.HCl+ 2,7-DAA-4,9-(Me)$_2$.HCl (unpurified mixture)

minimal inhibitory concentration (MIC) of <2.5 μg/mL.

Examples of MIC's of known antibiotic agents against S. aureus (taken from Antibiotics in Laboratory Medicine):

Penicillin: 8–16 μg/mL
Gentamicin: 0.25–16 μg/mL
Tetracycline: 0.5–32 μg/mL
Ciprofloxacin: 0.25–1 μg/mL

TABLE 1

RESULTS OF SOME BIOLOGICAL TESTING
IN MACRODILUTION ASSAY
Macrobroth Dilution Testing for Antimicrobial Activity
(Minimum Inhibitory Concentration in μg/mL)

| | Organism Used | | |
|---|---|---|---|
| Derivative No. | Escherichia coli ATCC 25922 | Staphlococcus aureus ATCC 25923 | Pseudomonas aeruginosa ATCC 27853 |
| 1 | 64.0 | 4.0 | >64 |
| 2 | >64 | 80.0 | >64 |
| 3 | >64 | 0.3 | >64 |
| 4 | >64 | >64 | >64 |
| 5 | >32 | >32 | >32 |
| 6 | 64.0 | 16.0 | 32.0 |
| 7 | 32.0 | 4.0 | 4.0 |
| 8 | 64.0 | 64.0 | >64 |
| 9 | — | — | — |
| 10 | >52 | >52 | >52 |

| Derivative No. | Compound |
|---|---|
| 1 | 1,8-DAA-3,6-(Me)$_2$ HCl |
| 2 | 1,8-DAA-3,6-(Me)$_2$ HCl + 2,7-DAA-4,9-(Me)$_2$ HCl (unpurified mixture) |
| 3 | 1,8-DAA-3,6-(Me)$_2$ HCl (from sublimed 1,8-DAA) |
| 4 | 1,8-DAA-3,6-(Me)$_2$ |
| 5 | 1,8-DAA-3,6-(Me)$_2$(N-Et)$_2$ PF$_6$ |
| 6 | 1,8-DAA-3,6-(Me)$_2$ norbornadiene |
| 7 | 1,8-DAA-3,6-(Me)$_2$(N-O)$_2$ |
| 8 | 1,8-DAA-3,6-(Me)$_2$(N-Me) BF$_4$ |
| 9 | 1,8-DAA-3,6-(Me)$_2$ maleic acid |
| 10 | Adduct of 1,8-DAA-3,6-(Me)$_2$ and K$_2$PtCl$_4$; product of Example 13. |

DISK SUSCEPTIBILITY ASSAY

Preparation of Plates

Mueller Hinton Agar (MHA) was prepared according to the manufacturers (BBL) directions and pipetted into 90 mm sterile petri dishes to a depth of 4 mm (requiring approximately 25 ml of agar per plate). Plates were allowed to solidify and refrigerated for a maximum of 2 weeks.

Preparation of Disks

Using grade No. 740E (Schleicher & Schuell, Keene, N.H.) 6 mm diameter filter paper disks (or equivalent), a known concentration of antibiotic test agent was applied in 20 μL aliquots to individual disks. Disks were air dried in a sterile hood for 2 hours and, if not being used immediately, stored in a desiccator at 4° C. until needed. The following dose schedule was used:

Concentration 6→2.5 g DAA+5 mL distilled water=10,000 μg/disk
Concentration 5→0.5 mL conc. 6+0.5 mL distilled H$_2$O=5,000 μg/disk
Concentration 4→0.5 mL conc. 5+0.5 mL distilled H$_2$O=2,500 μg/disk
Concentration 3→0.5 mL conc. 4+0.5 mL distilled H$_2$O=1,250 μg/disk
Concentration 2→0.5 mL conc. 3+0.5 mL distilled H$_2$O=625 μg/disk
Concentration 1→0.5 mL conc. 2+0.5 mL distilled H$_2$O=312.5 μg/disk Inoculum Preparation Using Trypticase Soy Agar (TSA) streak plates of test organisms (E. coli, S. aureus and P. aeruginosa), a sterile needle was inserted into several colonies of pure organism. This was transferred to tubes containing 0.5 mL of Trypticase Soy Broth (TSB) (one per test organism) using sterile technique. The tubes were inoculated at 35–37° C. for 4–6 hours to reach stationary phase of organism's growth curve. This inoculum was then diluted with distilled water 1:10 (inoculum: water) to achieve an approximation of the 0.5 McFarland turbidity standard (about $1\times10^8$ colony forming units (CFU)/mL).

Inoculation of Plates

MHA plates were inoculated using 0.5 mL TSB inoculi that were calibrated to match McFarlands standard. A sterile cotton swab was dipped into the inoculi and rotated against the side of the tube to remove excess. The swab was then streaked over the entire surface of the plate, rotated 60°, swabbed again, then rotated once more and swabbed a final time. This helped ensure a confluent growth of bacteria on the surface of the plate.

Application of Disks

Disks impregnated with known concentrations of antibiotic agent to be tested were applied to inoculated (swabbed) MHA plates. Disks were applied no more than 15 minutes after plate inoculation using sterile flamed forceps.

Controls

Gentamicin disks (10 μg/disk) were applied as positive controls.

Incubation of Plates

Inoculated plates with disks were incubated at 35–37° C. for 18 hours. Plates were placed flat on shelves to ensure that there was no variation in temperature amongst test plates (stacking of plates may cause a variation of as much as 4° C. between plates).

Reading of Results

Following 18 hour incubation, plates were removed from incubator and zones of inhibition around disks were measured to the nearest millimeter using a ruler. Results were recorded. A zone of inhibition of 15 mm or greater indicates that the organism is susceptible to test agent at that concentration.

| Concentration | Zone of Inhibition (in mm) |
|---|---|
| *S. aureus* against 1,8-DAA-3,6-(Me)$_2$HCl + 2,7-DAA-4,9-(Me)$_2$HCl (unpurified mixture) | |
| 312.5 | 15 |
| 625 | 18 |
| 1250 | 21 |
| 2500 | 23 |
| 5000 | 25 |
| 10000 | 28 |
| *E. coli* against 1,8-DAA-3,6-(Me)$_2$HCl + 2,7-DAA-4,9-(Me)$_2$HCl (unpurified mixture) | |
| 312.5 | 6 |
| 625 | 7 |
| 1250 | 9 |
| 2500 | 12 |
| 5000 | 17 |
| 10000 | 22 |
| *P. aeruginosa* against 1,8-DAA-3,6-(Me)$_2$HCl + 2,7-DAA-4,9-(Me)$_2$HCl (unpurified mixture) | |
| 312.5 | 6 |
| 625 | 6 |
| 1250 | 6 |
| 2500 | 7 |
| 5000 | 11 |
| 10000 | 16 |

The compound was also tested in the Standard Macrodilution Broth Protocol taken from *Antibiotics in Laboratory Medicine* (Lorian, V. (ed)(1991), Williams and Wilkins).

MICRODILUTION ASSAY

ANTIBACTERIAL PROPERTIES

Antibacterial properties against Gram positive and Gram negative organisms are demonstrated in the microbroth dilution assay of antimicrobial susceptibility, as adapted from *Antibiotics in Laboratory Medicine* (Lorian, V. (ed) (1991), Williams and Wilkins). It is described below, using *E. coli* ATCC® 25922, *S. aureus* ATCC® 25923, and *P. aeruginosa* ATCC® 27853.

Preparation of DAA Solution

Prepare 0.0128 g DAA in 10 mL dH$_2$O (or 95% EtOH, methanol or DMSO if H$_2$O insoluble)=1280 µg/mL (stock solution). Dilute DAA stock solution 1:10 with CAMHB (Cation-Adjusted Mueller Hinton Broth): 0.5 mL DAA stock solution+4.5 mL CAMHB=128 µg/mL (DAA working solution).

Preparation of Microtiter Plates

Pipette 100 µl of sterile CAMHB per well into columns 2–12 of rows A–G using Eppendorf repeater pipette. Pipette 100 µl per well of sterile-filtered DAA working solution into columns 1 and 2 of rows A, C, E, G using Jensen electric pipette. Mix and transfer 100 µl from column 2 to 3 of rows A, C, E, G using Jensen pipette. Repeat to column 12 then discard 100 µl from column 12.

| Resulting concentrations as follows: | |
|---|---|
| 1 = 64 µg/mL | 7 = 1.0 µg/mL |
| 2 = 32 µg/mL | 8 = 0.5 µg/mL |
| 3 = 16 µg/mL | 9 = 0.25 µg/mL |
| 4 = 8 µg/mL | 10 = 0.125 µg/mL |
| 5 = 4 µg/mL | 11 = 0.0625 µg/mL |
| 6 = 2 µg/mL | 12 = 0.0313 µg/mL |

Rows B, D and F are positive growth control lanes for each organism and contain only CAMHB and the organism—no DAA. Row H is the media additive control lane, if necessary (e.g. MeOH, EtOH, DMSO etc.). The concentration of the media additive is obtained by doing a 1:10 dilution of the additive with CAMHB (0.5 mL additive+4.5 mL CAMHB). Row G is considered to be "negative growth control" and is loaded with only CAMHB and the DAA.

Inoculum Preparation

Inoculate 0.5 mL TSB (Trypticase Soy Broth) tubes with 3 single colonies each of *E. coli*, *S. aureus*, and *P. Aeruginosa* from TSA plates using sterile needle. Incubate @ 37° C. for 4–6 hr.

Dilution of Inoculum

Measure out 100 mL CAMHB using the sterile 100 mL volumetric flask. Pour the excess into a sterile reagent reservoir. Pipette 0.5 mL and discard, leaving 99.5 mL in each of the 3-Erlenmeyer flasks. Set aside. Use the excess CAMHB for the 1:10 dilution of inoculum: 0.5 mL inoculum+4.5 mL CAMHB. Perform a 1:200 dilution of inoculum: 0.5 mL of 1:10 diluted inoculum+99.5 mL CAMHB from previous step.

Inoculation of Microtiter Plates

Pipette 100 µl (using Eppendorf repeater pipette) *E. coli* into each well in columns 1–12 of rows A and B and columns 1–4 of row H (if media additive control lane necessary). Pipette 100 µl *P. aeruginosa* into each well in columns 1–12 of rows C and D and columns 5–8 of row H (if media additive control lane is necessary). Pipette 100 µl *S. aureus* into each well in columns 1–12 of rows E and F and columns 9–12 of row H (if media additive control lane is necessary). Incubate microtiter plates @ 37° C. for 18 hrs.

Interpretation of Results

The lowest concentration of antimicrobial agent that results in significant inhibition of visible growth represents the MIC (Minimal Inhibitory Concentration).

Quality Control

Swab CAMHA (Cation-Adjusted Mueller Hinton Agar) plates (1 per organism) with *E. coli*, *S. aureus* and *P. aeruginosa*. Place disks of known antibiotic (Gentamicin 10 mcg—Lot #61147; Exp. November 97 (GM10)) onto swabbed plates. Incubate @ 37° C. for 18 hrs.

Control Limits for Gentamicin mcg 10:

*E. coli* ATCC® 25922 control zone diameter=19–26 mm

*S. aureus* ATCC® 25923=19–27 mm

*P. aeruginosa* ATCC® 27853=16–21 mm.

Results

Using the above protocol, MIC values of 64 µg/mL for 1,8-DAA-3,6-(Me)$_2$; 32 µg/mL for 1,8-DAA-3,6-(Me)$_2$·HCl; 0.125 µg/mL for 1,8-DAA-3,6-(Me)$_2$-N,N'-(O)$_2$; 1 µg/mL for 1,8-DAA-3,6-(Me)$_2$-5,10-(O)$_2$; 0.0625 µg/mL for the dimer product of Example 15; 64 µg/mL for 2,7-DAA-4,9-(Me)$_2$; were obtained versus *S. aureus*. An MIC of 4 µg/mL for 1,8-DAA-3,6-(Me)$_2$-N,N'-(O)$_2$ was obtained versus *E. coli*.

ANTIFUNGAL PROPERTIES

Compounds of the invention also display antifungal activities. These activities are demonstrated using an in vitro antifungal susceptibility assay adapted from the National Committee for Clinical Laboratory Standards (NCCLS). Using *C. albicans* ATCC® 90028, *C. neoformans* ATCC® 90112 and *T. glabrata* ATCC® 90030, the protocol is performed as follows:

Preparation of DAA Solution

Prepare 0.0128 g DAA in 10 mL $dH_2O$ (or other if $H_2O$ insoluble)=1280 μg/mL (stock solution). Dilute DAA stock solution 1:10 with RPMI-1640: 0.5 mL DAA stock solution+4.5 mL RPMI-1640=128 μg/mL (DAA working solution).

Preparation of Microtiter Plates

Inoculate rows A–H, columns 2–12 with 100 μl of RPMI-1640 using Eppendorf repeater pipette. Inoculate rows A–C columns 1 and 2 with 100 μl of 1st antibiotic (i.e. DAA-1) using electronic pipette. Inoculate rows E–G columns 1 and 2 with 100 μl of 2nd antibiotic (i.e. DAA-2) using electronic pipette. Serial dilute rows A–C and E–G using electronic pipette, obtaining desired drug concentrations. Plate is now ready for fungal inocula, which involves pipetting 100 μl of the inocula into all wells in rows A–C columns 1–12 and rows E–G columns 1–12.

Row D of each plate is dedicated for positive, negative, and additive controls of the first compound being tested, while row H is dedicated to controls for the second compound being tested and will be handled in the following manner:

Row D and row H, columns 2–4 (positive control), has 100 μl of fungal inocula added. Row D and row H, columns 6–8 (negative control), has 100 μl of drug being tested added. Row D and row H, columns 10–12 (additive control), has 80 μl of additional RPMI-1640 added and 20 μl of additive (ex. (Me)OH) added, thereby creating a 1:10 dilution for the additive control.

| Dilution factor: ex. starting with 128 μg/mL | |
|---|---|
| 1 = 64 μg/mL | 7 = 1.0 μg/mL |
| 2 = 32 μg/mL | 8 = 0.5 μg/mL |
| 3 = 16 μg/mL | 9 = 0.25 μg/mL |
| 4 = 8 μg/mL | 10 = 0.125 μg/mL |
| 5 = 4 μg/mL | 11 = 0.0625 μg/mL |
| 6 = 2 μg/mL | 12 = 0.0313 μg/mL |

Inoculum Preparation

Five colonies greater than 1 mm in diameter are suspended in a spectrophotometer cuvette containing 5 mL of sterile, 0.85% saline (colonies are obtained from 24 hrs. old Candida and Torulopsis cultures, while Cryptococcus colonies are chosen from 48 hrs. old cultures). Spectrophotometer is set to read % transmission at a wavelength of 530 nm, and is standardized using two cuvettes. Inocula suspension in cuvette is pipetted up and down several times to mix, placed into spectrophotometer where 90% transmission is sought. (90% transmission roughly equals $1 \times 10^6$ to $5 \times 10^6$-cells/mL). To obtain 90% transmission, suspension is diluted using the same 0.85% sterile saline, or if transmission exceeds 90%, additional fungi must be added. Once optimal inoculum cell density has been obtained further dilutions are performed using RPMI-1640. A 0.5 mL aliquot of stock suspension is mixed with 49.5 mL of RPMI-1640 in a 50 mL sterile Falcon tube, thus forming a 1:100 dilution of stock suspension. An additional 0.5 mL aliquot is taken from the 1:100 dilution and mixed with 9.5 mL of RPMI-1640 in a 15 mL sterile Falcon tube bringing the total volume to 10 mL; thus completing a 1:20 dilution of stock suspension with RPMI-1640. Fungal inoculum is now prepared and ready to be introduced to microplates. When larger volumes of inocula are required (due to increased numbers of DAA compounds being tested at one time) the final 1:20 dilution step uses proportionately increased volumes (i.e. 2.5 mL of fungal/RPMI-1640 is diluted in 47.5 mL of RPMI-1640).

Interpretation of Results

The lowest concentration of antimicrobial agent that results in significant inhibition of visible growth represents the MIC.

Results

Using the above protocol, MIC values of 32 μg/mL for 1,8-DAA-3,6-(Me)$_2$; 64 μg/mL for 1,8-DAA-3,6-(Me)$_2$.HCl; 8 μg/mL for 1,8-DAA-3,6-(Me)$_2$-5,10-(O)$_2$; were obtained versus *C. albicans*. MIC values of 4 μg/mL for 1,8-DAA-3,6-(Me)$_2$-5,10-(O)$_2$; 16 μg/mL for the product of Example 15; were obtained versus *C. neoformans*. MIC values of 4 μg/mL for 1,8-DAA-3,6-(Me)$_2$-5,10-(O)$_2$; 16 μg/mL for the dimer product of Example 15; were obtained versus *T. glabrata*.

ANTINEOPLASTIC PROPERTIES

As well, the invention exhibits in vitro anti-neoplastic activity against selected human cell lines. This activity was demonstrated using a fluorescence based live-cell/dead cell ratio in microscale using 96 well microtiter plates. Values of $IC_{50}$ (inhibitory concentration 50%) were calculated from the relative percent transmitted light as detected on a fluorescence 96 well plate reader.

| Compound | $IC_{50}$ in ug/mL Cell Line Used | | |
|---|---|---|---|
| | ZR-75-1 | ASPC-1 | 41-SK |
| 1,8-DAA(Me)$_2$ · HCl | 47.3 | 58.0 | 139.2 |
| 1,8-DAA(Me)$_2$(N-O)$_2$ | 1.9 | 9.3 | 11.3 |
| 1,8-DAA(Me)$_2$(N-Me)$_2$ | 38.3 | 62.5 | 35.9 |
| 1,8-DAA(Me)$_2$ · maleic acid | 46.9 | 62.5 | 44.3 |

The dimer product of Example 15 was subjected to various tests, as follows.

MATERIALS AND METHODS

The dimer product of Example 15 was obtained in powder form. A stock solution of 1280 mg/L of the dimer in dimethylsulfoxide (DMSO) was prepared and stored at room temperature in a foil-wrapped screw-capped tube (10 ml). Subsequent dilutions were prepared using cation-adjusted Mueller-Hinton broth (50 mg/L Mg). The dimer exhibited some precipitation upon dilution with MH broth after sitting for short periods of time. It was resuspended upon mixing each time an aliquot was taken from the solution.

DMSO was tested to confirm that it had no antibacterial activity.

Approximately 100 varied bacterial isolates were initially collected for screening, along with 9 ATCC organisms. Forty additional strains of Staphylococcus species were subsequently screened. All isolates were identified according to generally accepted lab protocol.

Broth microdilution was performed according to NCCLS guidelines. Microdilution panels were prepared using doubling dilutions of the dimer in ~250 μl plastic, 96-well trays. Inoculum suspension equal to a 0.5 McFarland standard were further diluted and added to the microdilution trays to achieve a final inoculum of $5 \times 10^5$ CFU/ml ($5 \times 10^4$ CFU/well). Colony counts were performed to confirm the final inoculum, as well as its purity. Each strain was also tested in a growth control well containing only MHB for viability.

Microdilution trays were incubated at 35° C. in ambient air or 5% $CO_2$ as appropriate for 16–20 hours. After incubation, the minimal inhibitory concentration (MIC) was defined as the lowest concentration of the dimer with no evidence of growth. Since 10 or more strains of most organisms were tested; a range of MICs was determined for each organism, as well as the concentration of the dimer that inhibited 50% of the strains (MIC50) and the concentration of the dimer that inhibited 90% of the strains (MIC90).

Various isolates were also tested for minimal bactericidal concentration (MBC) (see Tables D and F). The MBC is the lowest concentration of the dimer that shows a 99.9% reduction in the number of colonies from the initial inoculum.

During testing of the additional Staphylococcus species strains (see Table C), MICs appeared to be significantly higher than those tested in the original screen (see Table A). The dimer solution was two weeks old at this time. When the additional Staph strains were then retested using a freshly made solution of the dimer, the MICs were lower (see Table E). The stability of the solution stored at RT in a foil wrapped tube could be a variable contributing to the discrepancy between MICs.

Results are given in the following Tables.

TABLE A

Dimer
.0128 grams in 10 ml DMSO - 1280 mg/L
dilutions using MHB (cation supplemented)
*DMSO has no detectable antibacterial effect
*Some precipitation occurred at 128 mg/L. Resuspended upon mixing.

| Organism | # of Strains Tested | Range of MICs (mg/L) | MIC50 (mg/L) | MIC90 (mg/L) |
|---|---|---|---|---|
| Staph aureus | 12 | .0625–1.0 | 0.5 | 1.0 |
| Methicillin-resistant Staph aureus (MRSA) | 12 | 0.25–1.0 | 0.5 | 1.0 |
| Coagulase negative Staph (Staneg) | 10 | .0625–1.0 | 0.125 | 0.5 |
| Vancomycin susceptible Enterococcus (VSE) | 12 | 32>64 | >64 | >64 |
| Vancomycin resistant Enterococcus (VRE) | 12 | ≧64 | 64 | >64 |
| β strep grp A** | 10 | 32–64 | 32 | 64 |
| Strep pneumoniae** | 10 | 8–32 | 8 | 16 |
| P. aeruginosa | 10 | ≧64 | >64 | >64 |
| Enterobacteriaceae | 10 | >64 | >64 | >64 |
| B. cepacia | 5 | ≧64 | >64 | >64 |
| Acinetobacter | 5 | >64 | >64 | >64 |

| ATCC STRAINS | MIC (mg/L) |
|---|---|
| ATCC MSSA 25923 | 0.0625 |
| ATCC MSSA 29213 | 1.0 |
| ATCC MRSA 33591 | 0.5 |
| ATCC VRE 51299 | >64 |
| ATCC VSE 29212 | >64 |
| ATCC STRA 19615** | 32 |
| ATCC STRPNE 49619** | 2.0 |
| ATCC PA 27853 | >64 (x2) |
| ATCC EC 25922 | >64 |

**5% lysed horse blood in MHB (cation supplemented)

TABLE B

Dimer
1280 mg/L in DMSO, dilutions
using MHB (cation supplemented)

| Strain | 1st MIC | 2nd MIC |
|---|---|---|
| ATCC 25923 | | |
| S. aureus 1 | .0625 | .0625 |
| S. aureus 2 | 1.0 | 1.0 |
| S. aureus 3 | 0.5 | 0.125 |
| S. aureus 4 | 1.0 | 1.0 |
| S. aureus 5 | 1.0 | N/A mixed |
| S. aureus 6 | 0.125 | 0.25 |
| S. aureus 7 | 0.5 | 0.5 |
| S. aureus 8 | 0.5 | 1.0 |

TABLE C

Dimer
.0128 g in 10 ml DMSO stored at RT in foil wrapped tube = 1280 mg/L. Solution used in testing 14 days after preparation.
Dilutions prepared using cation adjusted MHB (Ca 50 mg/L, MG 25 mg/L).

| Organism | # of Strains | Range of MICs | MIC50 | MIC90 |
|---|---|---|---|---|
| S. aureus | 10 | 2–8 | 4 | 16 |
| Staneg | 10 | 0.25 > 16 | 1 | 2 |
| MRSA | 10 | >16 | >16 | >16 |
| Pip/Taz S. aureus | 10 | 2–16 | 2 | 8 |

| ATCC STRAINS | MICs |
|---|---|
| ATCC MRSA 33591 | 8, 16 |
| ATCC MSSA 25923 | 8, >16 |
| ATCC MSSA 29213 | 4, 8 |
| ATCC S. epid 14990 | 0.25 (x2) |

TABLE D

Dimer

\* = Skipped wells
- Subbed clear wells (50 µl)       Inoculum 5 × $10^4$/well
99.9% kill = 50 cols/well
Well = 100 µl
25 cols/50 µ1 = 99.9% kill

| Organism | MIC | MBC |
|---|---|---|
| S. aureus 1 | 2 | 2 |
| S. aureus 2 | 16 | >16 |
| S. aureus 3 | 8 | 16 |
| S. aureus 4 | 4 | 8 |
| S. aureus 5 | 16 | >16 |
| S. aureus 6 | 2 | >16* |
| S. aureus 7 | 8 | >16 |
| S. aureus 8 | 2 | >16* |
| S. aureus 9 | 2 | N/A |
| S. aureus 10 | 4 | N/A |
| Staneg | | |
| 1 | 2 | >16* |
| 2 | 0.25 | >4* |
| 3 | 2 | 16 |
| 4 | >16 | >16 |
| 5 | 1 | 16* |
| 6 | 1 | 8 |
| 7 | 1 | >16* |
| 8 | 1 | 16 |

TABLE E

Dimer
* = Skipped wells
Fresh solution used in testing same day. Same strains used in testing as with solution

| Organism | # of Strains | Range of MICs | MIC50 | MIC90 |
|---|---|---|---|---|
| S. aureus | 10 | 0.25–1 | 0.5 | 1 |
| Staneg | 10 | 0.0625–4 | 0.25 | 0.5 |
| MRSA | 10 | 0.5–8 | 2 | 8 |
| Pip/Taz SA | 10 | 0.25–2 | 1 | 2 |

| ATCC STRAINS | MICs |
|---|---|
| MRSA 33591 | 1.0 (×2) |
| MSSA 25923 | 0.125, 0.25 |
| MSSA 29213 | 2 (×2) |
| S. epid 14990 | 0.3125, 0.5* |

TABLE F

Dimer

\* = Skipped wells  Inoculum 5 × 10⁴/wells
- Subbed 50 µl of ≦5 clear wells
99.9% kill = 25 col/50 µl

| Organism | MIC | MBC |
|---|---|---|
| S. aureus 1 | 0.25 | 4* |
| S. aureus 2 | 1.0 | 1.0 |
| S. aureus 8 | 0.5 | ≧8* |
| Staneg 1 | 0.0625 | >1.0 |
| Staneg 4 | 4.0 | >16* |
| Staneg 7 | 0.25 | 1.0 |
| MRSA 2 | 8.0 | 16 |
| MRSA 4 | 2.0 | >16* |
| MRSA 6 | 0.5 | 2 |
| Pip/Taz S. aureus 1 | 2.0 | 8 |
| Pip/Taz S. aureus 3 | 0.25 | 4 |
| Pip/Taz S. aureus 7 | 1.0 | 2.0 |
| ATCC S. epid 14990 | 0.03125 | >0.5 |
| ATCC S. aureus 25923 | 0.25 | 4.0 |
| ATCC S. aureus 29213 | 2.0 | >16* |

TABLE G

Dimer

| Organism | # of Strains Tested | Range of MICs (mg/L) | MIC50 (mg/L) | MIC90 (mg/L) |
|---|---|---|---|---|
| S. aureus (2nd clinical isolate collection) | 10 | 0.25–1 | 0.5 | 1 |
| Coagulase negative staphylococci | 10 | 0.0625–4 | 0.25 | .5 |
| MRSA | 10 | 0.5–8 | 2 | 8 |
| * S. aureus (pip-tazo study) | 10 | 0.25–2 | 1 | 2 |

\* Comparative MICs available
ATCC 14990 (coag neg staph)
MIC 0.03125
MBC ≧0.5
ATCC 25923 (S. aureus) methicillin susceptible
MIC 0.25
MBC 4
ATCC 29213 (S. aureus) methicillin susceptible
MIC 2
MBC 16 (skipped wells)

We claim:

1. A 1,8-diazaanthracene compound of the formula I

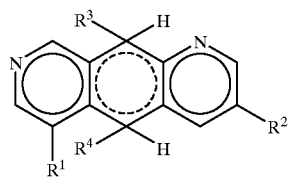

(I)

or a 2,7-diazaanthracene of formula (II)

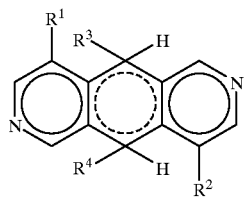

(II)

wherein the dotted line in the central ring indicates that either the central ring is aromatically unsaturated, and in this case either $R^3$ or H is absent from the 10-position and either $R^4$ or H is absent from the 5-position, or the central ring is saturated and $R^3$ and H and $R^4$ and H are present, or a corresponding 5,10-dione thereof, wherein $R^1$ and $R^2$, which are the same or different, are (a) straight-chained or branched alkyl, alkenyl or alkynyl groups whose carbon chain is optionally interrupted by one or several oxygen or sulphur atoms or one or several NH groups and which is unsubstituted or is substituted by one or more cycloalkyl, aryl, halogen, cyano, hydroxyl, acyloxy, amino, acylamino, monoalkylamino, dialkylamino, alkoxy, aryloxy, aralkoxy, carbamoyl, monoalkylcarbamoyl, dialkylcarbamoyl, carboxyl, alkoxycarbonyl, aryloxycarbonyl, aralkoxycarbonyl, crown ether or porphyrin groups;

(b) carboxyl;

(c) alkoxycarbonyl;

(d) aryloxycarbonyl;

(e) aralkoxycarbonyl;

(f) hydroxyl;

(g) alkoxy;

(h) aryloxy;

(i) aralkoxy;

(j) acyl;

(k) acyloxy (l) carbamoyl which is optionally mono- or di-alkyl substituted;

(m) formyl;

(n) aryl or (o) aralkyl;

and $R^3$ and $R^4$, if present, are the same or different and are hydrogen or take any of the values given for $R^1$ and $R^2$; or an N-oxide, N-halide, N-amine, salt, dimer, Diels-Alder adduct or carbene adduct thereof or a complex with a transition metal compound.

2. A compound as claimed in claim 1 that is of formula (I).

3. A compound as claimed in claim 1, wherein the central ring is aromatically unsaturated.

4. A compound as claimed in claim 1 wherein the central ring is aromatically unsaturated and $R^3$ and $R^4$ are both absent.

5. A compound as claimed in claim 1 wherein $R^1$ and $R^2$ are each alkyl, haloalkyl, aminoalkyl or carboxyl.

6. A compound as claimed in claim 1 in the form of an N-oxide, N-halide or quaternary ammonium salt.

7. A compound as claimed in claim 1, wherein $R^1$ and $R^2$ are each independently selected from the group consisting of methyl, chloromethyl, bromomethyl, iodomethyl, aminoethyl, carboxyl and alkoxycarbonyl groups.

8. A compound as claimed in claim 1, which is:

3,6-dimethyl-1,8-diazaanthracene, 3,6-di-α,α'-bromomethyl-1,8-diazaanthracene, 3,6-di-α,α'-chloromethyl-1,8-diazaanthracene, 3,6-di-α,α'-aminomethyl-1,8-diazaanthracene, 3,6-di-carboxyl-1,8-diazaanthracene, 3,6-dimethyl-1,8-diazaanthracene-N,N'-dibromide, 3,6-dimethyl-1,8-diazaanthracene-N,N'-dioxide, and salts thereof;

3,6-dimethyl-1,8-diazaanthracene-N,N'-di-($C_1$–$C_{20}$)alkyl quaternary salt wherein the counter ion is a halide, or a 5,10-dione thereof, 10,10'-bis(3,6-dimethyl-5,10-dihydro-1,8-diazaanthracen-5-one), or 5,5'-bis(3,6-dimethyl-5,10-dihydro-1,8-diazaanthracen-10-one.

9. A compound as claimed in claim 1 which is 3,6-dimethyl-1,8-diazaanthracene-5,10-dione.

10. A compound as claimed in claim 1 which is 3,6-dimethyl-5,10-dihydro-1,8-diazaanthracene.

11. A compound as claimed in claim 1 in the form of a Diels-Alder adduct with norbornadiene.

12. A compound as claimed in claim 1 in the form of a complex with a transition metal.

13. A compound as claimed in claim 1 in the form of a complex with a platinum compound.

14. A compound as claimed in claim 1 which is 4,9-dimethyl-2,7-diazaanthracene.

15. A compound as claimed in claim 1 which is a dimer of formula:

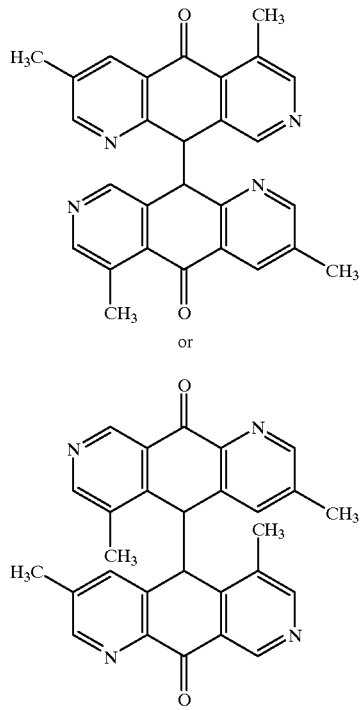

16. A pharmaceutical composition which comprises a pharmaceutically effective amount of compound as claimed in claim 1 in association with a pharmaceutically acceptable diluent or carrier.

17. A method of combating a bacterial illnesses in an animal which comprises administering to the animal in need thereof an antibacterially effective amount of a compound as claimed in claim 1, alone or in admixture with a pharmaceutically acceptable diluent or carrier.

18. A method of combating a fungal illnesses in an animal which comprises administering to the animal in need thereof an antifungally effective amount of a compound as claimed in claim 1, alone or in admixture with a pharmaceutically acceptable diluent or carrier.

19. A process for preparing 3,6-dimethyl-1,8-diazaanthracene and 4,9-dimethyl-2,7-diazaanthracene which comprises subjecting 3,5-lutidine to the effect of a strong reducing agent.

20. A process according to claim 19 wherein 3,5-lutidine is reacted with molten sodium to form 3,6-dimethyl-1,8-diazaanthracene and 4,9-dimethyl-2,7-diazaanthracene.

* * * * *

UNITED STATES PATENT AND TRADEMARK OFFICE
CERTIFICATE OF CORRECTION

PATENT NO : 5,994,365
DATED : November 30, 1999
INVENTOR(S) : Michael John Zaworotko; Subramanian Sethuraman Iyer It is certified that error appears in the above-identified patent and that said Letters Patent is hereby corrected as shown below:

In column 15, line 31, please delete "1H" and insert in lieu thereof --$^1$H--.

In column 15, line 49, please delete "(H20)" and insert in lieu thereof --($H_2O$)--.

In column 17, line 8, please delete "nmol" and insert in lieu thereof --mmol--.

In column 20, line 14, please delete "5,".

In column 20, line 15, please delete "000" and insert in lieu thereof --5,000--.

In column 20, line 16, please delete "2,".

In column 20, line 17, please delete "500" and insert in lieu thereof -- 2,500--.

In column 20, line 18, please delete "1,"

In column 20, line 19, please delete "000" and insert in lieu thereof --1,250--.

Signed and Sealed this

Fourteenth Day of November, 2000

*Attest:*

Q. TODD DICKINSON

*Attesting Officer*     *Director of Patents and Trademarks*